(12) United States Patent
Parums et al.

(10) Patent No.: US 6,794,192 B2
(45) Date of Patent: Sep. 21, 2004

(54) TARGET

(75) Inventors: Dinah Parums, Cambridge (GB); Stephen Charles Phillips, Kent (GB); John Ridden, Kent (GB)

(73) Assignee: Pfizer Inc., New York, NY (US)

( * ) Notice: Subject to any disclaimer, the term of this patent is extended or adjusted under 35 U.S.C. 154(b) by 362 days.

(21) Appl. No.: 09/894,743

(22) Filed: Jun. 28, 2001

(65) Prior Publication Data

US 2003/0040041 A1 Feb. 27, 2003

Related U.S. Application Data

(60) Provisional application No. 60/277,410, filed on Mar. 20, 2001.

(30) Foreign Application Priority Data

Jun. 29, 2000 (GB) ............................................. 0016009

(51) Int. Cl.[7] .............................................. G01N 31/00
(52) U.S. Cl. ......................... 436/15; 436/547; 435/7.21; 435/91.1; 435/240.27; 424/133.1; 424/134.1; 424/139.1; 424/146.1
(58) Field of Search .......................... 424/133.1, 134.1, 424/139.1, 146.1; 435/7.21, 240.27, 91.1; 436/547, 15

(56) References Cited

U.S. PATENT DOCUMENTS

| | | | |
|---|---|---|---|
| 5,702,936 A | | 12/1997 | Beavo et al. ................ 435/196 |
| 5,798,246 A | * | 8/1998 | Au-Young ................... 435/196 |
| 5,955,583 A | * | 9/1999 | Beavo et al. ............. 530/387.9 |
| 6,376,489 B1 | * | 4/2002 | Martins .................... 514/231.5 |

FOREIGN PATENT DOCUMENTS

| WO | WO 0033067 | 6/2000 | .......... G01N/33/00 |
|---|---|---|---|

OTHER PUBLICATIONS

Loughney, Kate, et. al., "Isolation and characterization of cDNAs encoding PDE5A, a human cGMP–binding, cGMP–specific 3',5'–cyclic nucleotide phosphodiesterase[1]," *Gene.*, vol. 216, No. 1, 1998, pp. 139–147.

Stacey, Peter, et. al., "Molecular Cloning and Expression of Human cGMP–Binding cGMP–Specific Phosphodiesterase (PDE5)[1]," *Biochemical and Biophysical Research Communications*, vol. 247, 1998, pp. 249–254.

Kotera, Jun, et al., "Genomic origin and transcriptional regulation of two variants of cGMP–binding cGMP–specific phosphodiesterases," *European Journal of Biochemistry*, vol. 262, No. 3, 1999, pp. 866–872.

Lin, Ching–Shwun, et. al., "Regulation of Human PDE5A2 Intronic Promoter by cAMP and cGMP: Identification of a Critical Sp1–Binding Site," *Biochemical and Biophysical Research Communications*, vol. 280, No. 3, 2001, pp. 693–699.

Lin, Ching–Shwun, et. al., "Expression of Three isoforms of cGMP–Binding cGMP–Specific Phosphodiesterase (PDE5) in Human Penile Cavernosum," *Biochemical and Biophysical Research Communications*, vol. 268, No. 2, 2000, pp. 628–635.

Charlton, Richard G., et. al., "LIP–1 (PDE–5A1); A Marker for Human Smooth Muscle Cells and Myofibroblasts," *Journal of Pathology.* vol. 192, 2000, pp. 27A.

\* cited by examiner

Primary Examiner—Long V. Le
Assistant Examiner—Jacob J. Cheu
(74) Attorney, Agent, or Firm—Gregory P. Raymer

(57) ABSTRACT

The present invention relates to an isolated target sequence. The target sequence is a splice variant of PDE5 called a PDE5*a*1, a component of which is presented as SEQ ID No 1. The identified target sequence of the present invention may be used to as a target to identify agents (such as modulators) useful in the prevention and/or treatment of a disease associated with scarring and/or fibrosis or to selectively identify smooth muscle cells and myofibroblasts and myoepithelial cells in samples of normal and diseased tissue from individuals.

2 Claims, 18 Drawing Sheets

Plate 1a
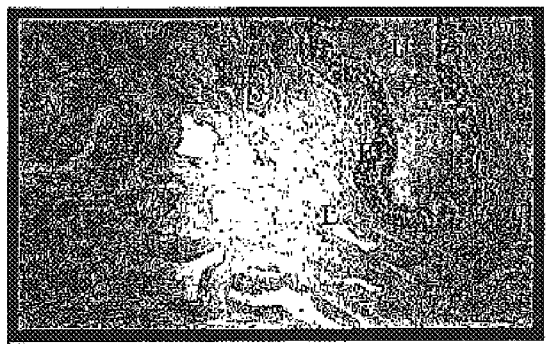
Plate 1b
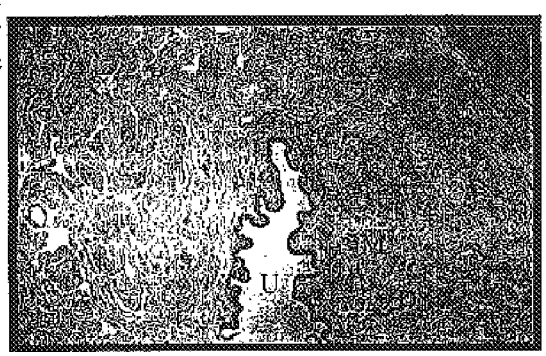
Plate 1c
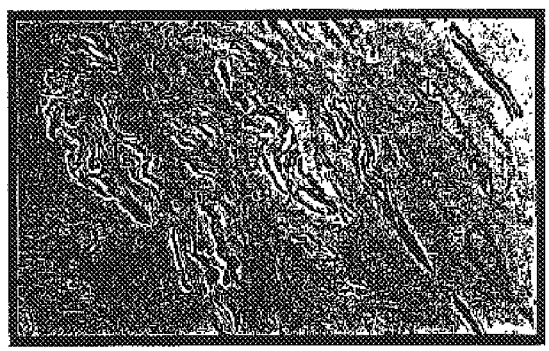
Plate 1d
Fig 1 (a-d)

Plate 2a
Plate 2b
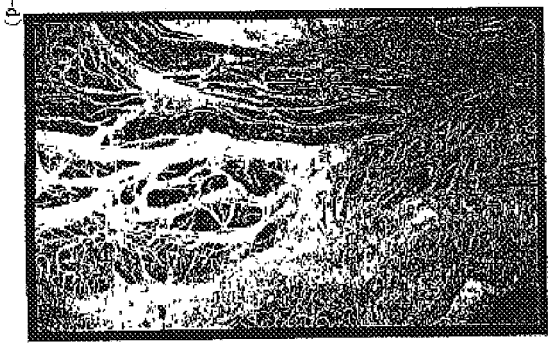
Plate 2c
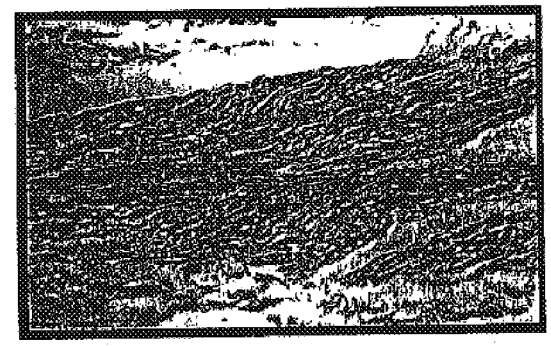
Plate 2d
Fig 2 (a-d)

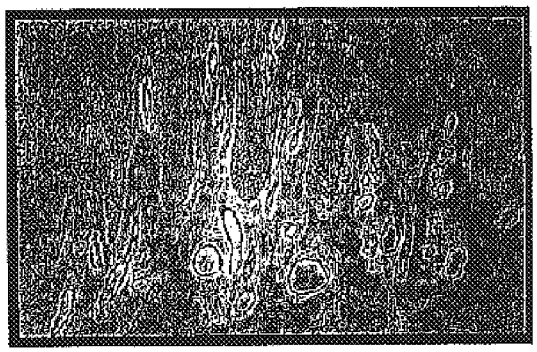
Plate 3a
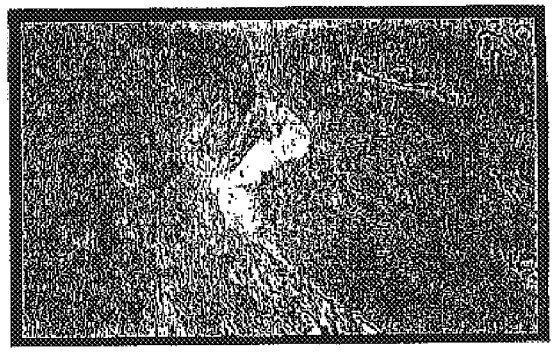
Plate 3b
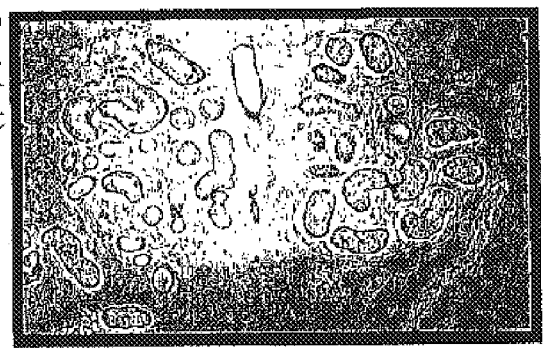
Plate 4a
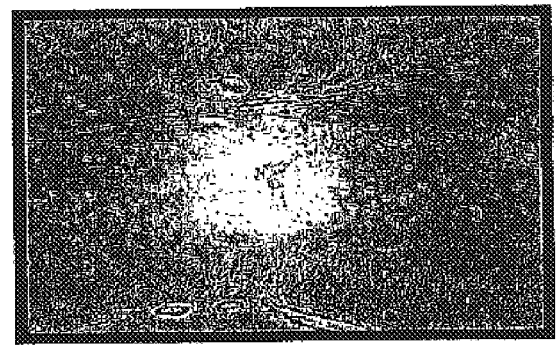
Plate 4b

Plate 5a
Plate 5b
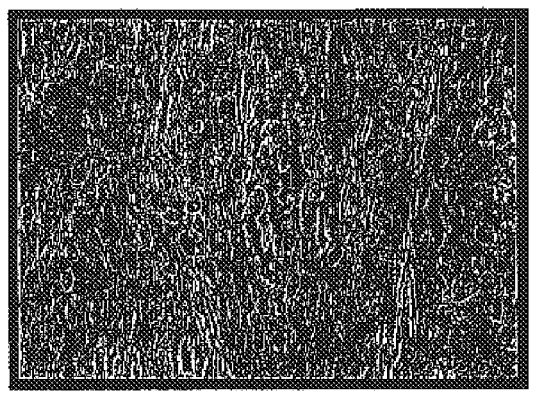
Plate 5c
Fig 5 (a-c)

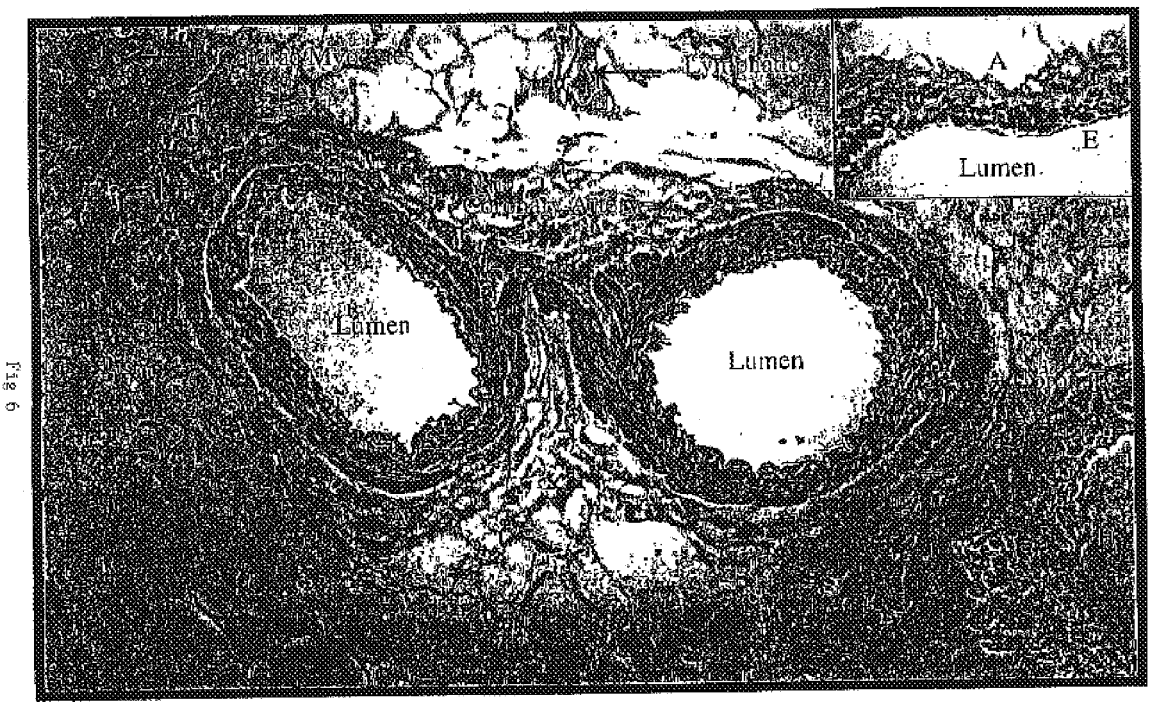
Plate 6.

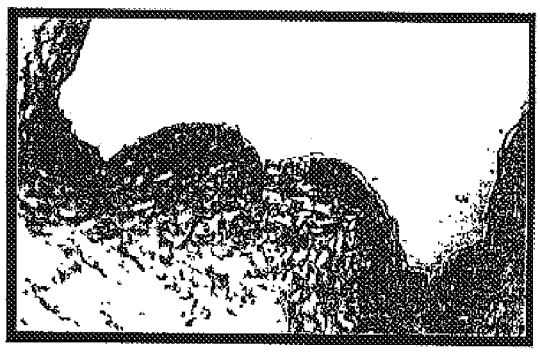
Plate 7a
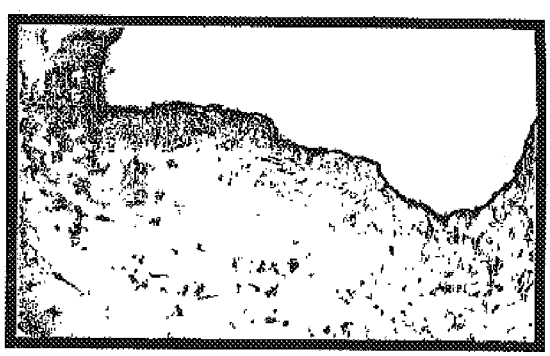
Plate 7b
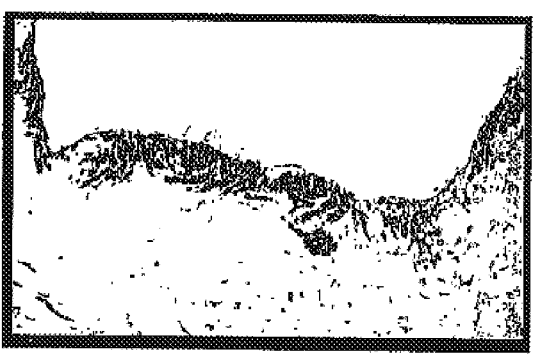
Plate 7c
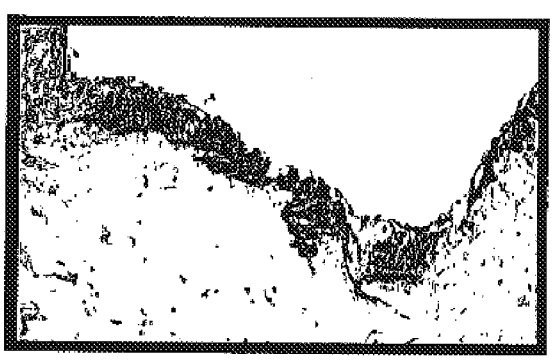
Plate 7d
Fig. 7 (a-d)

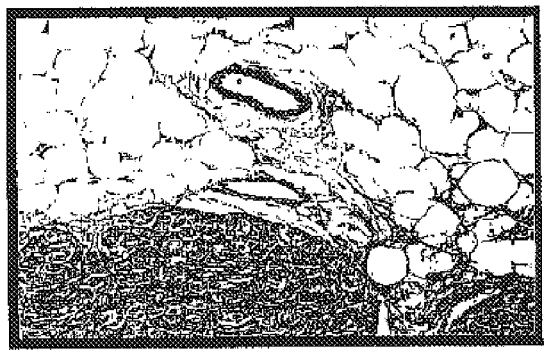
Plate 8a
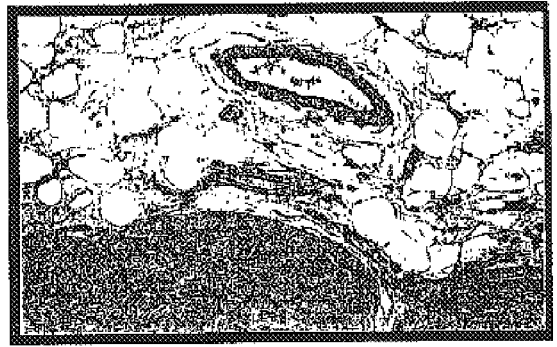
Plate 8b
Plate 8c
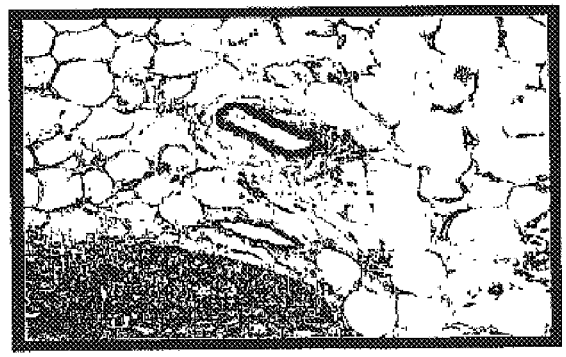
Plate 8d

Plate 9a
Plate 9b
Plate 10a
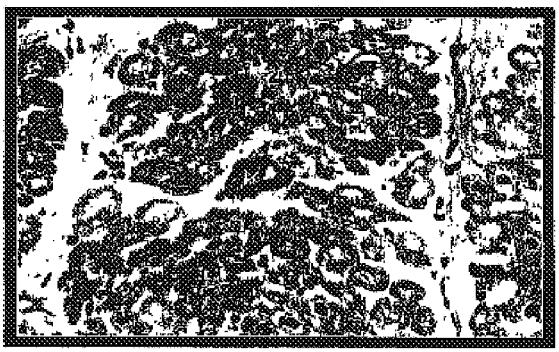
Plate 10b

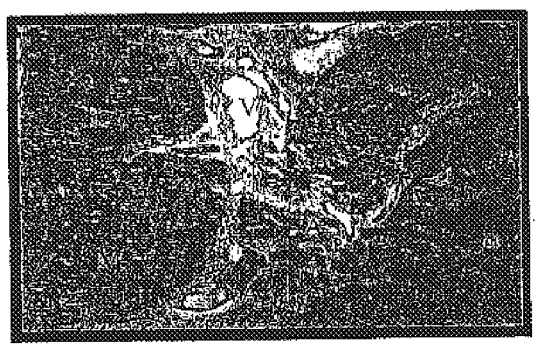
Plate 11a
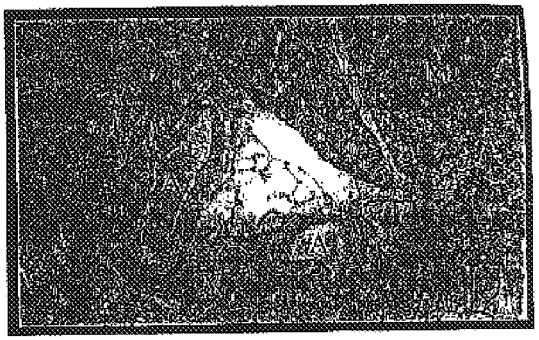
Plate 11b
Plate 11c
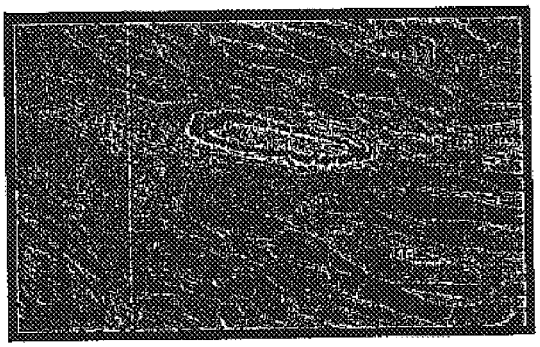
Plate 11d
Fig 11 (a-d)

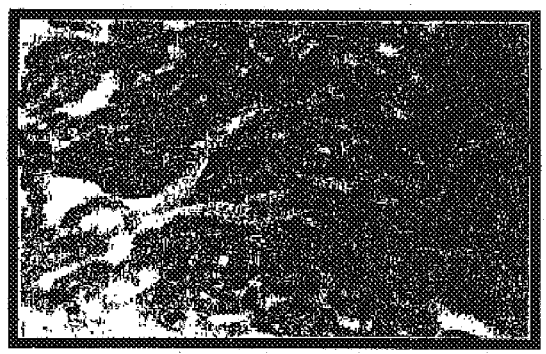
Plate 12a
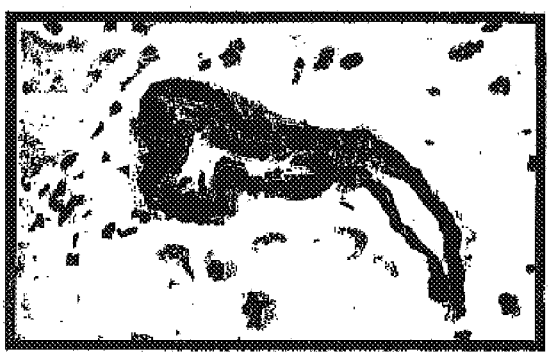
Plate 12b
Plate 12c
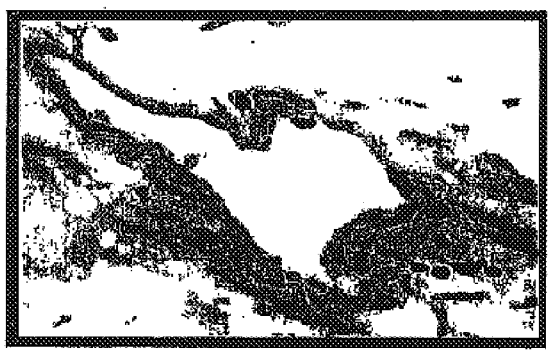
Plate 12d
Fig 12 (a-d)

Plate 13a
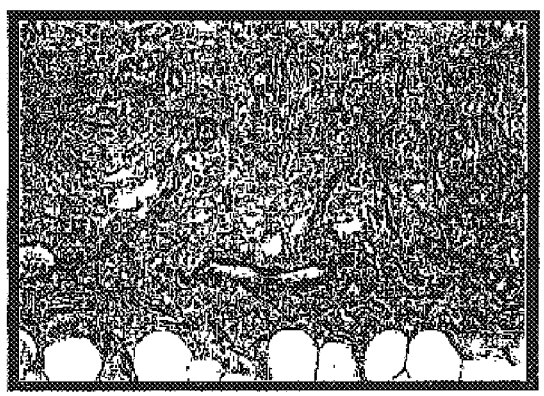
Plate 13b
Plate 13c
Fig 13 (a-c)

Plate 14a
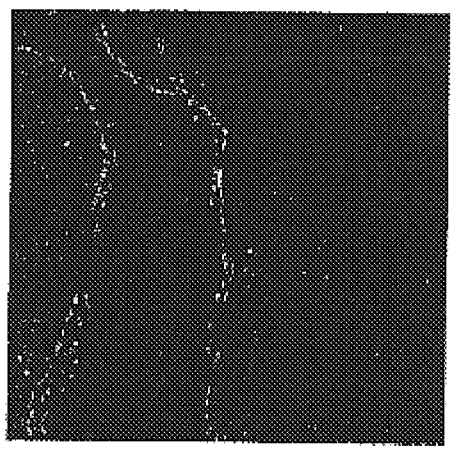
Plate 14b
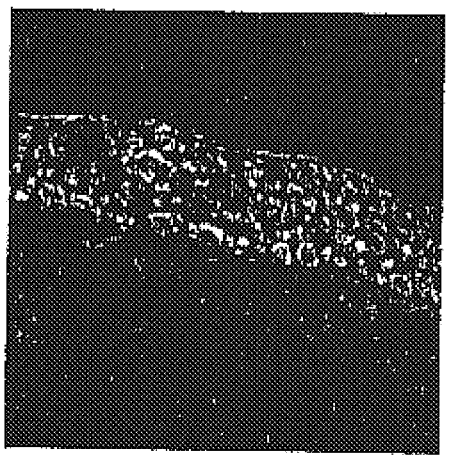
Plate 14c
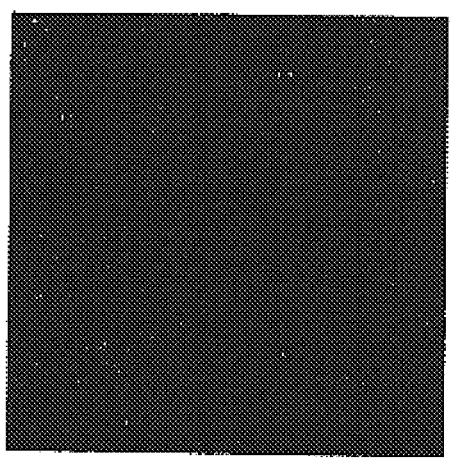
Plate 14d
Fig 14 (a-d)

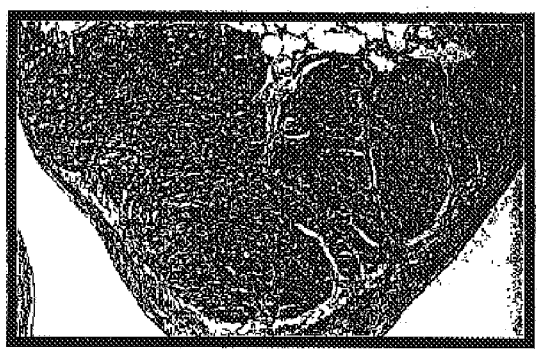
Plate 15a
Plate 15b
Plate 15c
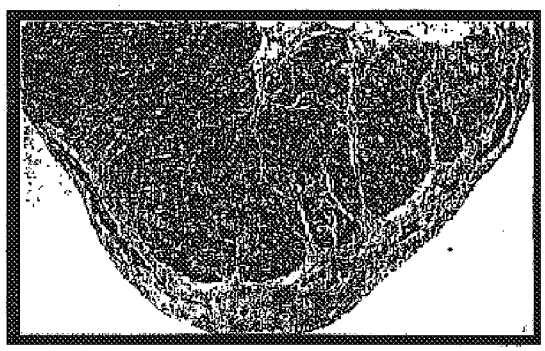
Plate 15d
Fig 15 (a-d)

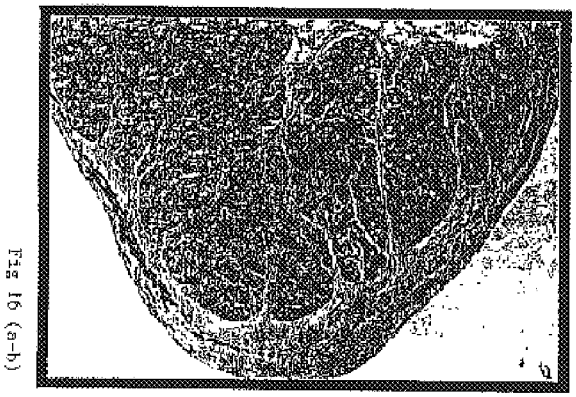 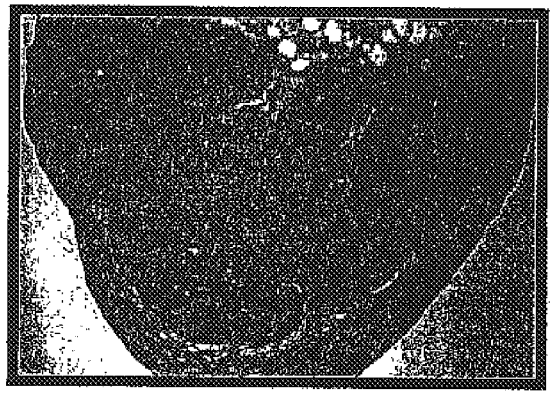
Plate 16a  Plate 16b

Plate 17a
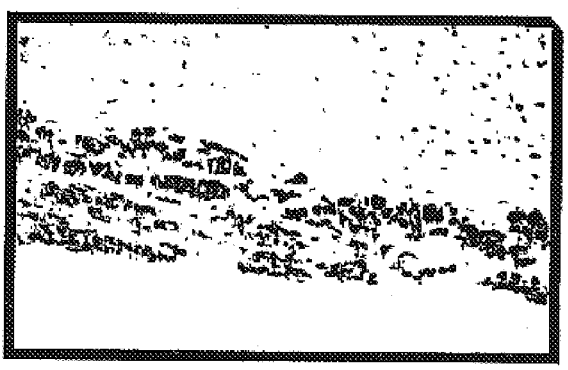
Plate 17b
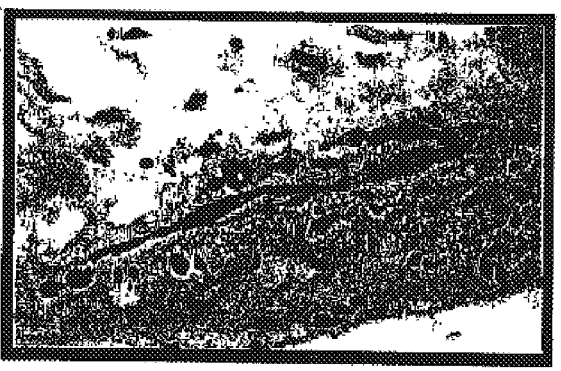
Plate 17c
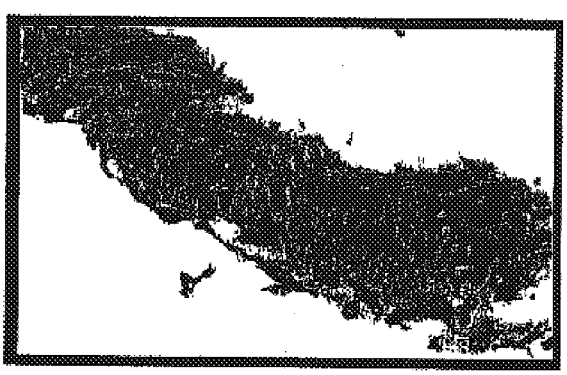
Plate 17d
Fig 17 (a-d)

Plate 18a
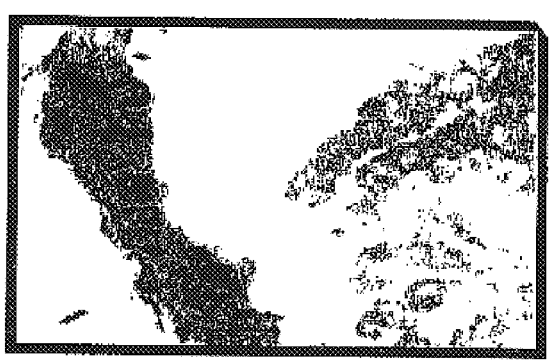
Plate 18b
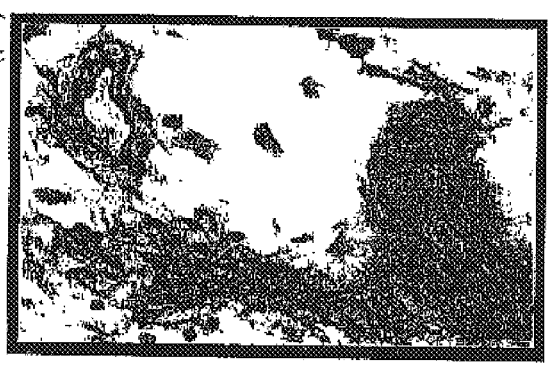
Plate 18c
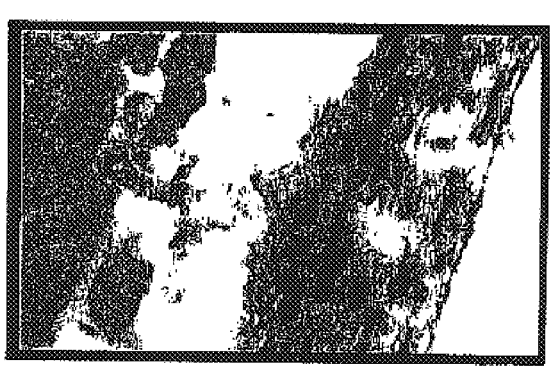
Plate 18d
Fig 18 (a-d)

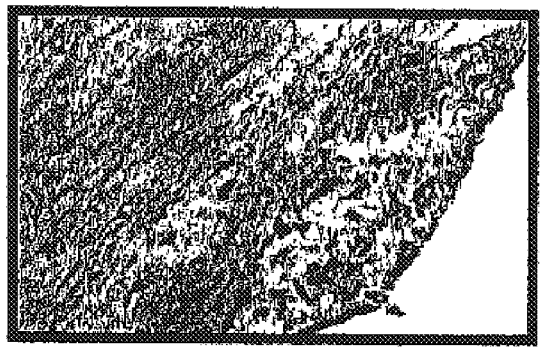
Plate 19a
Plate 19b
Plate 19c
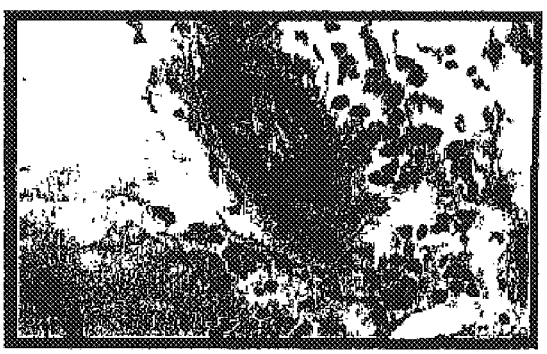
Plate 19d
Fig 19 (a-d)

Plate 20a
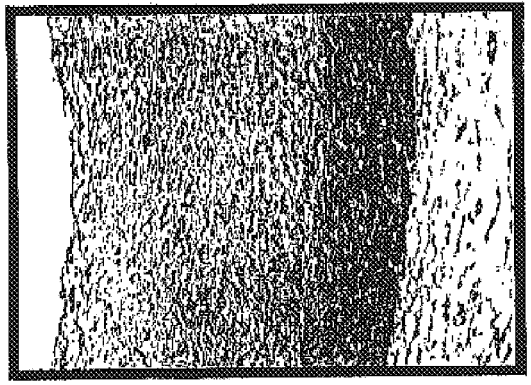
Plate 20b
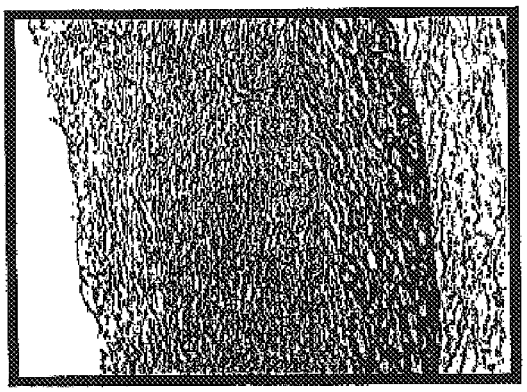
Plate 20c
Fig 20 (a-c)

SEQUENCE LISTING

<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

Met Glu Arg Ala Gly Pro Ser Phe Gly Gln Gln Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide
<221> NAME/KEY: MISC_FEATURE
<222> LOCATION: (1)..(13)
<223> OTHER INFORMATION: man-made there are no n's or x's in
      the sequence

<400> SEQUENCE: 2

Met Glu Arg Ala Gly Pro Ser Phe Gly Gln Gln Arg Cys
1               5                   10

TARGET

CROSS REFERENCE TO RELATED APPLICATION

This application claims the benefit of United Kingdom Application No. 0016009.3 filed Jun. 29, 2000 and U.S. Application No. 60/277,410 filed Mar. 20, 2001.

The present invention relates to an isolated target sequence. In particular the present invention relates to a method for the diagnosis of a disease or a predisposition to a disease by screening for the presence of the target sequence. More in particular, the present invention relates to the diagnosis of a disease or a predisposition to disease associated with scarring and/or fibrosis. In accordance with the present invention, examples of disease associated with scarring and/or fibrosis include (but are not necessarily limited to): lung fibrosis, atherosclerosis, cardiovascular disease, dermal and corneal scarring and/or fibrosis following infection, trauma, surgery or thermal injury, scleroderma and other connective tissue disorders, fibrosis of the heart, chronic obstructive pulmonary disease, muscle fibrosis, kidney fibrosis, chronic dermal ulceration and lipodermatosclerosis, lung fibrosis (of any origin), post-surgical and idiopathic adhesions, inflammatory conditions of the skin (including Lichen and associated conditions), ageing and all ageing-associated degenerative disorders (including ageing of the skin), liver fibrosis of any ethiology (including viral and non-viral hepatitis), liver cirrhosis, chronic pancreatitis, chronic thyroiditis, calcinosis (of any origin), conditions whose pathogenesis is related to the deposition/modelling of a connective matrix (including cancer). In addition, the present invention relates to a kit for diagnosis for susceptibility or predisposition to a number of disorders, including disorders associated with scarring and/or fibrosis, and to components for inclusion in said kit. The present invention relates to the use of the isolated target sequence to evaluate and/or screen for agents capable of interacting with same. The present invention further provides a means for the directed treatment of such disease states.

BACKGROUND TO THE INVENTION

The incidence of some diseases associated with scarring and/or fibrosis is a significant drain on resources in both developing and developed nations. By way of example, some diseases associated with scarring and/or fibrosis may manifest themselves in the form of atherosclerosis and cardiovascular disease. These diseases are of particular relevance to public health. By way of example, it has been estimated that atherosclerosis leads to approximately 500,000 deaths from coronary artery disease and 150,000 deaths from stroke (Ml) every year in the United States (American Heart Association, 1996). It is now known that atherosclerosis is the principal cause of myocardial infarction, stroke, and peripheral vascular disease, accounting for nearly half of all mortality in developed countries.

The costs for both national and international public health programmes attempting to deal with the consequences of these diseases are substantial. It would therefore be desirable to provide a means for screening individuals to identify those who are predisposed to disease associated with scarring and/or fibrosis and especially to identify to which scarring and fibrotic diseases they are susceptible.

At present, treatment of diseases associated with scarring and/or fibrosis can be effective in slowing the progression of the disease, but only after the disease has been diagnosed. However, such treatments are seldom capable of reversing the effects of the disease once it has set in. Prophylactic treatment of the general population is expensive and a significant drawback is that such treatments are not targeted to the needs of the individual and may be either redundant or even counterproductive. In some cases adverse side effects may be experienced from prolonged exposure to inappropriate prophylactic treatments.

The progression of certain diseases associated with scarring and/or fibrosis such as atherosclerosis, may involve the accumulation/proliferation of smooth muscle cells (SMCs) which elaborate extracellular matrix macromolecules which are largely collagenous in nature. The progression of atherosclerosis from thrombosis to myocardial infarction (MI) can lead to tissue injury which may result in both scar tissue turnover and fibrous tissue formation. Although the process of normal would repair after tissue injury results in the proliferation of fibroblast cell, the differentiation of fibroblasts into myofibroblasts can mark an early event in the development of tissue fibrosis. The prolonged presence of myofibroblasts at an infarct site may also likely to produce an imbalance in extracellular matrix proteins and proteases, which may exacerbate hypertrophic scars and wound formation.

It would be desirable to have a method for diagnosis of disease associated with scarring and/or fibrosis and/or a predisposition to disease associated with scarring and/or fibrosis that solves or at least ameliorates the disadvantages associated with the prior art.

It would also be advantageous to be able to identify new therapeutic targets which would facilitate the identification with increased accuracy of those individuals having a predisposition or increased susceptibility to diseases associated with scarring and/or fibrosis which are associated with an accumulation/proliferation of smooth muscle cells (SMCs) and/or a prolonged presence of myofibroblasts at a disease site. In this way, suitable therapy could then be put into place before the effects of such a disease sets in.

SUMMARY ASPECTS

The present invention relates to methods for inter alia identifying and/or diagnosing the presence or absence of one or more target sequences in a sample taken from an individual. In particular, these methods relate to screens to determine the presence or absence of a target sequence. The methods of the present invention may also be used to determine the relative position of multiple target sequences in a sample taken from an individual order to provide a risk profile for that individual. The identified target sequence may be used to diagnose a disease associated with scarring and/or fibrosis and/or predisposition to a disease associated with scarring and/or fibrosis by correlating the identified target sequence with inherited genetic factors and/or phenotypic traits. The identified target sequence may also be used as a target for the discovery of agents (such as modulators) which may be effectively used to prevent or delay or treat a disease associated with scarring and/or fibrosis or a predisposition to a disease associated with scarring and/or fibrosis associated with these target sequence.

In a broad sense, the present invention relates to an assay method for detecting the presence of a target sequence presented as SEQ ID No 1 or an analogue thereof wherein the assay method comprises a means for detecting said target sequence.

DETAILED ASPECTS OF THE INVENTION

According to a first aspect of the present invention, there is provided an isolated target sequence wherein the target sequence is presented as SEQ ID No 1.

In this embodiment, typically the target sequence is taken from an individual or is in a sample taken from an individual. In this embodiment, typically the individual is a human.

In this embodiment, typically the target sequence is associated with (e.g. located in or on) cells that express a smooth muscle phenotype.

In a highly preferred aspect, the target sequence is associated with (e.g. located in or on) actin intermediate filaments.

In a highly preferred aspect, the target sequence is associated with (e.g. located in or on) a smooth muscle cell and/or a myofibroblast and/or a myoepithelial cell.

According to a second aspect of the present invention there is provided a moiety, such as an antibody, capable of recognising a target sequence wherein the target sequence is presented as SEQ ID No 1.

According to a third aspect of the present invention there is provided an assay method for detecting the presence of a target sequence in a cell or tissue sample from an individual, wherein the target sequence is presented as SEQ ID No 1, and wherein the assay method comprises:
(i) contacting the cell with a moiety, such as an antibody, capable of recognising the target sequence under conditions that could permit binding of the moiety to the target sequence; and
(ii) detecting the presence of the moiety bound to the target sequence.

According to a fourth aspect of the present invention there is provided a method of diagnosis for a disease or a predisposition to a disease associated with the presence of a target sequence in a cell or a tissue sample from an individual wherein the method comprises:
(i) performing the assay method of the present invention and
(ii) determining whether the cell or tissue comprises the target sequence.

According to a fifth aspect of the present invention there is provided a method for preventing and/or treating a disease or a predisposition to a disease associated with the presence of a target sequence in a cell or tissue from an individual; wherein the method comprises:
(i) performing the assay method of the present invention;
(ii) determining whether the cell or tissue comprises a target sequence; and
applying a treatment in order to prevent, delay, reduce or treat the disease or the predisposition to the disease if said cell or tissue comprises a target sequence.

According to a sixth aspect of the present invention there is provided a kit for diagnosis of a disease or a predisposition to disease, wherein the kit comprises:
(i) means for identifying a target sequence presented as SEQ ID No 1; and
(ii) reference means for determining the selectivity of the identifying means.

According to a seventh aspect of the present invention, there is provided an amino acid sequence comprising an antigenic determinant wherein said antigenic determinant is that of or contained within SEQ ID No 1.

According to a eighth aspect of the present invention, there is provided the use of a target sequence in the preparation of a medicament to prevent and/or treat disease associated with scarring and/or fibrosis.

According to a eighth aspect of the present invention, there is provided an assay method for detecting the presence of a target sequence in a cell or tissue sample from an individual wherein the assay method comprises:

(iii) contacting the cell with an antibody of the present invention under conditions that could permit binding of the antibody to the cell; and
(iv) detecting the presence of the antibody bound to the cell.

Other aspects of the present invention are presented in the accompanying claims and in the following description and drawings. These aspects are presented under separate section headings. However, it is to be understood that the teachings under each section are not necessarily limited to that particular section heading.

Preferable Aspects

For some embodiments, preferably the treatment is for a disease associated with scarring and/or fibrosis.

Preferably the treatment is or comprises treatment with a phosphodiesterase (PDE) inhibitor.

Preferably the invention provides for diagnosis or predisposition to a disease associated with scarring and/or fibrosis.

Preferably the invention provides for a nucleotide sequence encoding an amino acid sequence comprising an antigenic determinant wherein said antigenic determinant is that of or contained within SEQ ID No 1.

Surprising Findings

The present invention is based on the surprising findings that:
(i) the target sequence may be used as a marker to selectively identifying cells expressing a smooth muscle type in samples of normal and diseased tissue from an individual;
(ii) the target sequence may be used as a marker to selectively identifying smooth muscle cells and myofibroblasts and myoepithelial cells in samples of normal and diseased tissue from an individual;
(ii) the target sequence was not an obvious choice as a target sequence as it is one or two splice variants, and we found that the other one of which is not specifically expressed on smooth muscle cells and myofibroblasts and myoepithelial cells; and
(iii) the target sequence of the present invention comprises a clinically useful antigenic determinant which is highly immunologically reactive.

Antigenic Determinant

The term "antigenic determinant" as used herein refers to a site on anantigen which is recognised by an antibody or T-cell receptor. Typically, it is a short peptide derived from or as part of a protein antigen.

Immunologically Reactive

As used herein, "immunologically reactive" is defined as the capability of the natural, recombinant or synthetic target sequence of the present invention to induce a specific immune response in appropriate animals or cells and to bind with specific antibodies.

Target Sequence

As used herein, the term "target sequence" refers to the N-terminal sequence of a human phosphodiesterase enzyme termed PDE5A1 which is part of the long splice variant of PDE5a. In particular, the target sequence of the present invention is a short segment of the long form of the splice variant of PDE5a1 presented in SEQ ID No. 1 as MERAGPSFGQQR. The target sequence comprises an antigenic determinant/epitope which is immunologically reactive and which provides a means for identifying the target sequence in a sample from an individual. This target sequence is readily detectable in tissue such as but not limited to bladder, colon, lung, pancreas, placenta, prostate, corpus cavernosum, small intestine, stomach and coronary heart tissue using an antibody raised against the target sequence.

Phosphodiesterases (PDEs)

Cyclic nucleotide phosphodiesterases (PDEs; EC 3.1.4.17) are a superfamily of enzymes that catalyze the hydrolysis of 3-prime,5-prime-cyclic nucleotides to the corresponding nucleoside 5-prime-monophosphates. The PDEs have been subdivided into several families on the basis of sequence, substrate specificity, kinetic properties, and regulatory features. Each family and even members with a family exhibit distinct tissue, cell and subcellular expression patterns and hence participate in discrete signal transduction pathways.

PDE5

The PDE5 family is of particular interest. The members of the PDE5 family are cGMP-binding, cGMP-specific enzymes which are involved in the NO/cGMP signalling pathway which modulates smooth muscle tone. Sildenafil (Viagra™, UK-92, 480) is an orally active PDE5 inhibitor which is efficacious in the treatment of male erectile dysfunction by potentiating NO mediated increases in cGMP in corpus cavernosal smooth muscle.

PDE5 Splice Variants

By screening several human cDNA libraries with a bovine PDE5 cDNA, Loughney et al. (1998) (Loughney, K.; Hill, T. R.; Florio, V. A.; Uher, L.; Rosman, G. J.: Wolda, S. L.; Jones, B. A.; Howard, M. L.; McAllister-Lucas, L. M.; Sonnenburg, W. K.; Fancis, S. H.; Corbin, J. D.; Beavo, J. A.; Ferguson, K.: Gene 216: 139–147, 1998) isolated cDNAs encoding human PDE5A. Northern blot analysis revealed that PDE5A was expressed in various human tissues such as aortic smooth muscle, heart, placenta, skeletal muscle and pancreas and to a much lesser extent in brain, liver and lung. Two different splice variants that encode PDE5A proteins with different amino termini were isolated. These splice variants were named PDE5A1 and PDE5A2. The predicted 875-amino acid PDE5A1 human protein was shown to be approximately 96% identical to bovine PDE5A. Like the bovine PDE5A protein, human PDE5A1 contained a cGMP-binding domain in its N-terminal portion and a catalytic domain in its C-terminal region. Recombinant PDE5A1 protein hydrolyzed cGMP in vitro. Loughney et al. (1998) (ibid) also isolated an alternatively 5' spliced variant termed PDE5A2. The cDNA the encodes a 833 amino acid PDE5A2 protein with a differing N terminus (eight amino acids are substituted for the amino-terminal 50 amino acids of PDE5A1).

Independently, Stacey et al. (1998) (Stacey, P.; Rulten, S.; Dapling, A.; Phillips, S. C.: Biochem. Biophys. Res. Commun. 247: 249–254, 1998) also cloned PDE5A cDNAs and demonstrated using Northern Blot analysis the existence of at least two splice variants of the PDE5A protein. The human PDE5 cDNA was isolated and shown to contain an open reading frame encoding an 875 amino acid, 100,012Da polypeptide, the expression of which yielded a protein of the predicted size and capable of hydrolyzing cGMP. The deduced amino acid sequence was very similar (95%) to that of bovine PDE5, and comprised a conserved cGMP-binding domain and catalytic domain. Northern analysis revealed a major and minor transcript of approximately 9 kb and approximately 8 kb respectively, thus indicating the existence of at least two splice variants, the major form being readily detected in bladder, colon, lung, pancreas, placenta, prostate, small intestine, and stomach.

Yanaka et al (1998) (Yanaka, N.; Kotera, J.; Ohtsuka, A.; Akarsuka, H.; Imai, Y.; Michibata, H.; Fujishige, K.; Kawai, E.; Takebayashi, S.1.; Okumura, K.; Omori, K.: Eur. J. Biochim. 255: 391–399, 1998) reported on the tissue-specific expression of PDE5A mRNA in human tissues. The PDE5A transcripts were detected in adult lung, fetal lung, and pulmonary smooth muscle cells (SMCs) indicating an important role of PDE5A in modulating pulmonary vasoconstriction. Yanaka et al (1998) also demonstrated that PDE5A mRNA was significantly produced in human whole heart. In particular cultured coronary SMCs produced the PDE5A transcripts, which suggested that PDE5A mRNa was concentrated in coronary artery.

Workers such as Stacey et al (ibid) have suggested that PDE5A splice variants may: (a) play a role in regulating enzyme stability and (b) influence the activity and location of the PDE5 enzyme by conferring an ability on the enzyme to assocated with specific cellular membranes. Other workers such as Yanaka et al (ibid) have suggested that although PDE5A may play a physiological roles in the human cardiovascular system, further investigations were needed to: (i) determine the precise cellular distribution of the PDE5A transcript in human tissues; and (ii) to assess whether disorder of regulation of intracellular cGMP level or abnormal PDE5A expression in human cardiac tissue is associated with cardiac disorders/cardiovascular disease.

Advantages

The present invention is advantageous because it:
(i) provides a new therapeutic target which facilitates the determination of the precise cellular distribution of the PDE5A1 transcript in human tissues.
(ii) allows for screening for target sequences in samples from an individual. The availability of such a screen is advantageous as it provides for a more accurate diagnosis of normal and diseased states and/or a predisposition to disease states and conditions.
(iii) facilitates the identification with increased accuracy of those individuals having a predisposition or increased susceptibility to a disease associated with scarring and/or fibrosis.
(iv) allows for the identification of individuals who have an increased risk of developing such disease associated with scarring and/or fibrosis. A suitable therapy may then be put in place to prevent or treat or delay the onset of these diseases.
(vi) helps to identify patients most likely to respond positively to treatment with certain classes of therapies or particular therapeutics.
(vii) allows for the selection of optimal clinical trial patient samples thereby reducing the size of a trial and/or decreasing the time of the clinical trial.
(viii) allows for the identification of agents capable of modulating the onset of a disease associated with scarring and/or fibrosis.
(ix) provides an agent that would aid in the understanding of a pathological disease state using an immunological approach.

Other advantages are discussed and are made apparent in the following commentary.

Myofibroblast

In one embodiment, the method of the present invention allows for the identification of myofibroblasts in a sample from an individual. In this regard, the development of a method to diagnose the presence of myofibroblast cells with a view to providing a treatment to reduce the myofibroblast cell number would be a useful strategy for providing effective and efficient treatment of scar tissue.

As used herein, the term "myofibroblast" refers to a cell type derived from the mesoderm which is usually found at sites of scarring and inflammation. These cells are thought to be derived from fibroblasts but show phenotypicsmc differentiation The myofibroblast differs from the fibroblast in that it has a highly organised cytoskeleton. The myofibroblast is recognised to be involved in wound healing and fibroblastic proliferations. It is involved in collagen production but may also possess intraceullular microfilaments which provide the myofibroblasts with motile (rather than contractile) properties. Myofibroblasts are bipolar cells with ultrastructural features that include abundant intracytoplasmic rough endoplasmic reticulum, the cisternae of which are filled with finely granular electron dense material. A small number of intracytoplasmic mitochondria, a prominent Golgi apparatus, free ribosomes, occasional pinocytotic vesicles and microtubules may be present. Intracytoplasmic bundles of electron-dense actin-like microfilaments measuring up to 6–8 nm in diameter, with focal condensations or 'dense bodies' and occasional desmosomes. A basal lamina is present around most myorfibroblast cells is characteristically incomplete or 'clumped' around the cell borders. The nuclei have a smooth nuclear membrane and finely dispersed chromatin. The myofibroblast is often associated with mature and immature collagen and can express vimentin, alpha smooth muscle actin.

Smooth Muscle Tissue

In one embodiment, the method of the present invention allows for the identification of smooth muscle tissue in a sample from an individual.

The term "smooth muscle" means muscle lacking striations, hence giving it a smooth appearance. It is also called involuntary muscle. An increase in the concentration of $Ca^{2+}$ in smooth muscle cytosol initiates contraction, just as in striated muscle. However, sarcoplasmic reticulum (the reservoir for $Ca^{2+}$ in striated muscle) is scant in smooth muscle. Thus, calcium ions flow into smooth muscle cytosol from both the extracellular fluid and sarcoplasmic reticulum, but because there are no transverse tubules in smooth muscle fibres, it takes longer for $Ca^{2+}$ to reach the filaments in the centre of the fibre and trigger the contractile process. This accounts, in part, for the slow onset and prolonged contraction of smooth muscle.

Smooth Muscle Cells (SMCs)

In one embodiment, the method of the present invention allows for the identification of smooth muscle cells in a sample from an individual. In this regard, smooth muscle tissue is composed of smooth muscle fibres (cells) which are located in the walls of hollow internal organs and innervated by autonomic motorneurons.

As used herein, the term "smooth muscle cell (SMC)" refers to a cell type derived from the mesoderm having a highly organised cytoskeleton. SMCs are bipolar and can exist in two forms, contractile and secretory. In this regard, a contractile SMC comprises ultrastructural features which include abundant intracytoplasmic myofilaments with few organelles although a few peri-nuclear and peripheral mitochondria are present with small clusters of ribosomes.

A secretory SMC comprises ultrastructural features which include a well developed rough endoplasmic reticulum and Golgi complex resulting in compression of the myofilaments to the periphery of the cell. A secretory SMC makes collagen, proteoglycans and elastic fibre proteins and can express vimentin, alpha smooth muscle actin, myosin and desmin.

It has been shown 'modified' smooth muscle cells in the intima of arteries and arterioles and in ageing and failing cardiac endocardium have been shown to express the target.

Myoepithelial Cells

In one embodiment, the method of the present invention allows for the identification of myoepithelial cells (MECs) in a sample from an individual. In this regard, the development of a method to diagnose the presence of myoepithelial cells with a view to providing a treatment to reduce the myoepithelial cell number would be a useful strategy for providing effective and efficient treatment of scar tissue.

Myoepithelial cells express a smooth muscle phenotype and are seen around the ducts of glands and are found in breast, prostate and skin. Thesemyoepithelial cells are differentiated smooth muscle cells. Informationon MECs has been reported by:

Nayar R, Breland C, Bedrossian U, Masood S, DeFrias D, Bedrossian C W: Ann Diagn Pathol 1999 Jun. 3(3):165–73 "Immunoreactivity of ductal cells with putative myoepithelial markers: A potential pitfall in breast carcinoma."

Damiani S, Ludvikova M, Tomasic G, Bianchi S, Gown AM, Eusebi V: Virchows Arch 1999 Mar;434(3):227–34 "Myoepithelial cells and basal lamina in poorly differentiated in situ duct carcinoma of the breast. An immunocytochemical study."

Prasad M L, Hyjek E, Giri D D, Ying L, O'Leary J J, Hoda S A:Am J Surg Pathol 1999 Feb. 23(2):176–81 "Double immunolabeling with cytokeratin and smooth-muscle actin in confirming early invasive carcinoma of breast."

Savera A T, Gown A M, Zarbo R J: Mod Pathol 1997 Nov. 10(11):1093–100 "Immunolocalization of three novel smooth muscle-specific proteins in salivary gland pleomorphic adenoma: assessment of the morphogenetic role of myoepithelium."

Kohnen G, Castellucci M, Hsi B L, Yeh C J, Kaufmann P: Cell Tissue Res 1995 Aug;281(2):231–42 "The monoclonal antibody GB 42—a useful marker for the differentiation of myofibroblasts."

Mosunjac M B, Lewis M M, Lawson D, Cohen C: Diagn Cytopathol 2000 Sep. 23(3):151–5 "Use of a novel marker, calponin, for myoepithelial cells in fine-needle aspirates of papillary breast lesions."

Contraction and Relaxation

Several mechanisms regulate contraction and relaxation of smooth muscle cells. In one, a regulatory protein called calmodulin binds to $Ca^{2+}$ in the cytosol. Not only do calcium ions enter smooth muscle fibres slowly, but they also move slowly out of the muscle fibre when excitation declines, which delays relaxation. The prolonged presence of $Ca^{2+}$ in the cytosol provides for smooth muscle tone, a state of continued partial contraction. Smooth muscle tissue is located in the walls of hollow internal organs such as but not limited to blood vessels, airways to the lungs, the stomach, intestinal gall bladder, urinary bladder, the corpus cavernosa of the penis and the clitoris.

Diagnostic Kits

In one embodiment, the present invention also includes a diagnostic composition or diagnostic methods or kits for (i) detection and measurement of a target sequence in biological fluids and tissue; and/or (ii) localization of a target sequence in a sample from an individual; and/or for (iii) the detection of a predisposition to a disease, such as a disease associated with scarring and/or fibrosis. In this respect, the composition or kit will comprise an entity that is capable of indicating the presence of one or more—or even the absence of one or more targets in a test sample. The kit of the present invention may also comprise reference means.

As used herein, the term "reference means" refers to reference samples and/or control samples.

As used herein, the term "tissue" means a collection of cells organised to perform one or more specific functions. The tissue may be derived from the walls of hollow internal organs such as but not limited to blood vessels, airways to the lungs, the stomach, intestinal gall bladder, urinary bladder, the corpus cavernosa of the penis and the clitoris. The term "tissue" includes tissue extracts, cultured tissue samples (including disrupted versions thereof) and tissue sections.

In one embodiment, preferably, the test sample is obtained from male or female sexual genitalia or a secretion thereof or therefrom.

Assay Methods

The diagnostic compositions and/or methods and/or kits may be used in the following techniques which include but are not limited to; competitive and noncompetitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, immunohistochemistry and immunocytochemistry. By way of example, an immunohistochemistry kit may also be used for localization of the target sequence in smooth muscle cells. This immunohistochemistry kit permits localization of the target sequence in tissue sections and cultured cells using both light and electron microscopy which may be used for both research and clinical purposes. Such information may be useful for diagnostic and possibly therapeutic purposes in the detection and/or prevention and/or treatment of diseases associated with scarring and/or fibrosis. For each kit the range, sensitivity, precision, reliability, specificity and reproducibility of the assay are established. Intraassay and interassay variation is established at 20%, 50% and 80% points on the standard curves of displacement or activity.

Diagnostic Testing

In order to provide a basis for the diagnosis of disease, normal or standard values from a target should be established. This may be accomplished by combining body fluids or cell extracts taken from normal subjects, either animal or human, with, for example, an antibody to a target under conditions suitable for complex formation which are well known in the art. The amount of standard complex formation may be quantified by comparing it to a dilution series of positive controls where a known amount of antibody is combined with known concentrations of a purified target. Then, standard values obtained from normal samples may be compared with values obtained from samples from subjects potentially affected by a disease, such as a disease associated with scarring and/or fibrosis. Deviation between standard and subject values establishes the presence of the disease state.

The assay methods of the present invention may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for target expression should be established. This is accomplished by combining body fluids or cell extracts taken from normal subjects, either animal or human, with the target or a portion thereof, under conditions suitable for detection of the target sequence. Standard quantification may be carried out by comparing the values obtained for normal subjects with a dilution series of positive controls run in the same experiment where a known amount of purified target is used. Standard values obtained from normal samples may be compared with values obtained from samples from subjects potentially affected by a disorder or disease related to expression of the target coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, in one aspect, the present invention relates to the use of a target sequenceper se or the use of a target sequence to produce anti-target antibodies which can, for example, be used diagnostically to detect and quantify the levels of the target sequence in disease associated with scarring and/orfibrotic states.

The present invention further provides diagnostic assays and kits for the detection of a target in cells and tissues comprising a purified target which may be used as a positive control, and anti-target antibodies. Such antibodies may be used in solution-based, membrane-based, or tissue-based technologies to detect any disease state or condition related to the expression of target protein or expression of deletions or a variant, homologue, fragment or derivative thereof.

The diagnostic compositions and/or kits comprising these entites may be used for a rapid, reliable, sensitive, and specific measurement and localization of a target sequence in tissue extracts. In certain situations, the kit may indicate the existence a disease associated with scarring and/or fibrosis.

Reporters

A wide variety of reporters may be used in the assay methods (as well as screens) of the present invention with preferred reporters providing conveniently detectable signals (eg. by spectroscopy). By way of example, a reporter gene may encode an enzyme which catalyses a reaction which alters light absorption properties.

Examples of reporter molecules include but are not limited to 1-galactosidase, invertase, green fluorescent protein, luciferase, chloramphenicol, acetyltransferase, β-glucuronidase, exo-glucanase and glucoamylase. Alternatively, radiolabelled or fluorescent tag-labelled nucleotides can be incorporated into nascent transcripts which are then identified when bound tooligonucleotide probes.

In one preferred embodiment, the production of the reporter molecule is measured by the enzymatic activity of the reporter gene product, such asp-galactosidase.

A variety of protocols for detecting and measuring the expression of the target, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on the target is preferred, but a competitive binding assay may be employed. These and other assays are described, among other places, in Hampton R et al (1990, Serological Methods, A Laboratory Manual, APS Press, St Paul Minn.) and Maddox DE et al(1983, J Exp Med 15 8:121 1).

A wide variety of labels and conjugation techniques are known by those skilled in the art and can be used in various nucleic and amino acid assays. Means for producing labelled hybridisation or PCR probes for detecting the target polynucleotide sequences include oligolabelling, nick translation, end-labelling or PCR amplification using a labelled nucleotide. Alternatively, the target coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Isolated Target Sequence

For some aspects of the present invention, the target sequence of the present invention is an isolated target sequence.

As used herein, the term "isolated" is used interchangeably with the term "purified" or "non-native". The isolated target sequence of the present invention may be in a substantially isolated form. It will be understood that the target sequence may be mixed with carriers or diluents which will not interfere with the intended purpose of the target sequence and still be regarded as substantially isolated. The target sequence of the present invention may also be in a substantially purified form, in which case it will generally comprise the target sequence in a preparation in which more than 90%, e.g. 95%, 98% or 99% of the target sequence in the preparation is a peptide comprising the amino acid sequence set out in SEQ ID No 1.

Amino Acid Sequences

As used herein, the term "amino acid sequence" refers to peptide, polypeptide sequences, protein sequences or portions thereof.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

The amino acid sequence may be prepared isolated from a suitable source, or it may be made synthetically, such as by chemical synthetic methods or it may be prepared by use of recombinant DNA techniques.

Typically the target sequence of the present invention will be prepared by chemical synthesis techniques.

Target Sequence

The target sequence (which is presented as SEQ ID No 1) is the amino acid sequence MERAGPSFGQQR.

Amino Acid Codes

The one-letter amino acid symbols recommended by the IUPAC-IUB Biochemical Nomenclature Commission are indicated as follows. The three-letter codes are also provided for reference purposes.

| A | Ala | Alanine |
|---|-----|---------|
| C | Cys | Cysteine |
| D | Asp | Aspartic acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

As used herein, SEQ ID No 1 which is presented as MERAGPSFGQQR means the sequence per se or an analogue thereof—for example, a chemical analogue thereof.

As used herein, the term "chemical analogue" means a compound that is structurally similiar to SEQ ID No 1.

In one aspect, the present invention provides an target sequence which is capable of acting as a target in an assay for the identification of one or more agents and/or derivatives thereof capable of affecting the target sequence in order to modulate the activity of the target sequence.

The sequence may be used in screens to identify agents capable of modulating target sequence activity. In this regard, a target sequence may comprise the amino acid sequence as set out in SEQ ID No 1 or a nucleotide sequence encoding which is prepared by recombinant and/or synthetic means or an expression entity comprising same.

Alternatively, the target sequence may be suitable tissue extract comprising target sequence or an equivalent thereof.

The target may even be a combination of such tissue and/or recombinant targets.

Screens

Test agents capable of modulating the activity of the target sequence may be screened in assays, which are well known in the art. Screening may be carried out, for example in vitro, in cell culture, and/or in vivo. Biological screening assays may be based on but not limited to activity-based response models, binding assays and bacterial, yeast and animal cell lines (which measure the biological effect of an agent in a smooth muscle cell, such or a tissue extract comprising same). The assays can be automated for high capacity-high throughput screening (HTS) in which large numbers of compounds can be tested to identify compounds with the desired target sequence modulating activity (see, for example WO 84/03564). Once an agent capable of modulating the target sequence activity—has been identified, further steps may be carried out either to select and/or to modify compounds and/or to modify existing compounds, to improve the target sequence modulation capability.

Chemical Synthesis Methods

Typically the agent of the present invention will be prepared by chemical synthesis techniques.

The agent of the present invention or variants, homologues, derivatives, fragments or mimetics thereof may be produced using chemical methods to synthesize the agent in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Direct synthesis of the agent or variants, homologues, derivatives, fragments or mimetics thereof can be performed using various solid-phase techniques (Roberge J Y et al (1995) Science 269: 202–204) and automated synthesis may be achieved, for example, using the ABI 43 1 A Peptide Synthesizer (Perkin Elmer) in accordance with the instructions provided by the manufacturer. Additionally, the amino acid sequences comprising the agent or any part thereof, may be altered during direct synthesis and/or combined using chemical methods with a sequence from other subunits, or any part thereof, to produce a variant agent.

In an alternative embodiment of the invention, the coding sequence of the agent or variants, homologues, derivatives, fragments or mimeticsthereof may be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

Agent

As used herein, the term "agent" includes any entity capable of modulating the activity of a sequence comprising the target sequence of the present invention.

Modulating

The term "modulating" includes but is not limited to any treatment which may prevent, suppress, alleviate, restorate, elevate or modify the expression and/or activity of a sequence comprising the target sequence of the present invention.

By way of example, the agent of the present invention can include but is not limited to a target sequence activator, agonist, enhancer or upregulator which increases the target sequence activity. The agent may also be an antagonist acts directly or indirectly on another entity (or target) which is capable of inhibiting/impairing the target sequence activity.

As used herein, the term "agent" includes, but is not limited to, a compound which may be obtainable from or produced by any suitable source, whether natural or not. The agent may be designed or obtained from a library of compounds which may comprise peptides, as well as other compounds, such as small organic molecules and particularly new lead compounds. By way of example, the agent may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a derivatised agent, a peptide cleaved from a whole protein, or a peptides synthesised synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof. The agent may even be a target sequence or an amino acid sequence comprising same or a nucleotide sequence encoding same or a variant, homologue or derivative thereof or a functional equivalent thereof (such as a mimetic) or a combination of agents as outlined above.

As used herein, the term "agent" may be a single entity or it may be a combination of agents.

Hence, the agent can be an amino acid sequence or a chemical derivative thereof. The substance may even be an organic compound or other chemical. The agent may even be a nucleotide sequence—which may be a sense sequence or an anti-sense sequence. The agent may even be an antibody.

If the agent is an organic compound then for some applications that organic compound will typically comprise one or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

The agent may contain halo groups. Here, "halo" meansfluoro, chloro, bromo or iodo.

The agent may contain one or more of alkyl, alkoxy, alkenyl, alkylene and alkenylene groups—which may be unbranched- or branched-chain.

The agent may be in the form of a pharmaceutically acceptable salt—such as an acid addition salt or a base salt—or a solvate thereof, including a hydrate thereof. For a review on suitable salts see Berge et al, J. Pharm. Sci., 1977, 66, 1–19.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

A pharmaceutically acceptable salt of an agent of the present invention may be readily prepared by mixing together solutions of the agent and the desired acid or base, as appropriate. The salt may precipitate from solution and be collected by filtration or may be recovered by evaporation of the solvent.

The agent of the present invention may exist in polymorphic form.

The agent of the present invention may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of a compound of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{31}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

It will be appreciated by those skilled in the art that the agent of the present invention may be derived from a prodrug. Examples of prodrugs include entities that have certain protected group(s) and which may not possess pharmacological activity as such, but may, in certain instances, be administered (such as orally or parenterally) and thereafter metabolised in the body to form the agent of the present invention which are pharmacologically active.

It will be further appreciated that certain moieties known as "pro-moieties", for example as described in "Design of Prodrugs" by H. Bundgaard, Elsevier, 1985 (the disclosure of which is hereby incorporated by reference), may be placed on appropriate functionalities of the agents. Such prodrugs are also included within the scope of the invention.

The agent of the present invention may also be capable of displaying one or more other beneficial functional properties. By way of example, the agent of the present invention may potentiate cAMP and/or potentiate cGMP.

Preferably the agent may selectively agonise, and/or selectively upregulate or selectively inhibit a suitable target.

Agonist

In one embodiment of the present invention, preferably the agent is selected from the group consisting of an agonist, a partial agonist and a competitive agonist of the target sequence.

As used herein, the term "agonist" means any agent which is capable of increasing a proportion of the target sequence that is in an active form, resulting in an increased biological response. The term includes partial agonists and inverse agonists.

Partial Agonist

As used herein, the term "partial agonist" means an agonist that is unable to evoke the maximal response of a biological system, even at a concentration sufficient to saturate the specific receptors.

Inverse Agonist

As used herein, the term "partial inverse agonist" is an inverse agonist that evokes a submaximal response to a biological system, even at a concentration sufficient to saturate the specific receptors. At high concentrations, it will diminish the actions of a full inverse agonist.

Antagonist

As used herein, the term "antagonist" means any agent that reduces the action of another agent, such as an agonist. The antagonist may act at on the same target as the agonist. The antagonistic action may result from a combination of the substance being antagonised (chemical antagonism) or the production of an opposite effect through a different target (functional antagonism or physiological antagonism) or as a consequence of competition for the binding site of an intermediate that links target activation to the effect observed (indirect antagonism).

Antibodies

In one embodiment of the present invention, preferably the agent of the present invention is an antibody.

For the purposes of this invention, the term "antibody", unless specified to the contrary, includes but is not limited to, polyclonal, monoclonal, chimeric, single chain, Fab fragments and fragments produced by a Fab expression library. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Furthermore, the antibodies and fragments thereof may be humanised antibodies. Neutralizing antibodies, i.e., those which inhibit biological activity of the substance polypeptides, are especially preferred for diagnostics and therapeutics.

Antibodies may be produced by standard techniques, such as by immunisation with the substance of the invention or by using a phage display library.

If polyclonal antibodies are desired, a selected mammal (e.g., mouse, rabbit, goat, horse, etc.) is immunised with an immunogenic polypeptide bearing a epitope(s) obtainable from an identified agent and/or substance of the present invention. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed if purified the substance polypeptide is administered to immunologically compromised individuals for the purpose of stimulating systemicdefence.

Serum from the immunised animal is collected and treated according to known procedures. If serum containing polyclonal antibodies to an epitope obtainable from an identifed agent and/or substance of the present invention contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against epitopes obtainable from an identifed agent and/or substance of the present invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies to the substance and/or identified agent of the present invention may be prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946, 779) can be adapted to produce the substance specific single chain antibodies.

Antibodies, both monoclonal and polyclonal, which are directed against epitopes obtainable from an identifed agent and/or substance of the present invention are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for the substance may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al(1989) Science 256:1275–128 1).

Mimetic

The agent of the present invention may be a mimetic.

As used herein, the term "mimetic" relates to any chemical which includes, but is not limited to, a peptide, polypeptide, antibody or other organic chemical which has the same qualitative activity or effect as a known agent.

Derivative

The term "derivative" or "derivatised" as used herein includes chemical modification of an agent. Illustrative of such chemical modifications would be replacement of hydrogen by a halo group, an alkyl group, an acyl group or an amino group.

Chemical Modification

In one embodiment of the present invention, the agent may be a chemically modified agent.

The chemical modification of an agent of the present invention may either enhance or reduce hydrogen bonding interaction, charge interaction, hydrophobic interaction, Van Der Waals interaction or dipole interaction between the agent and the target.

In one aspect, the identified agent may act as a model (for example, a template) for the development of other compounds.

Recombinant Methods

Typically the agent of the present invention is prepared by recombinant DNA techniques.

Preferably the nucleotide sequence encoding the agent of the present invention is introduced into a vector and expressed under in vitro, and/or in vivo and/or ex vivo conditions.

Nucleotide Sequence

As used herein, the term "nucleotide sequence" is synonymous with the term "polynucleotide".

The nucleotide sequence may be DNA or RNA of genomic or synthetic or of recombinant origin. The nucleotide sequence may be double-stranded or single-stranded whether representing the sense orantisense strand or combinations thereof. For some applications, preferably, the nucleotide sequence is DNA.

For some applications, preferably, the nucleotide sequence is prepared by use of recombinant DNA techniques (e.g. recombinant DNA).

For some applications, preferably, the nucleotide sequence iscDNA.

For some applications, preferably, the nucleotide sequence may be the same as the naturally occurring form.

Vector

In one embodiment of the present invention, the agent be administered directly to an individual.

In another embodiment of the present invention, a vector comprising a nucleotide sequence encoding an agent administered to an individual.

Preferably the agent prepared and/or delivered to a target site using a genetic vector.

As it is well known in the art, a vector is a tool that allows or faciliates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences of the present invention and/or expressing the proteins of the invention encoded by the nucleotide sequences of the present invention. Examples of vectors used in recombinant DNA techniques include but are not limited to plasmids, chromosomes, artificial chromosomes or viruses.

The term "vector" includes expression vectors and/or transformation vectors.

The term "expression vector" means a construct capable of in vivo or in vitro/ex vivo expression.

The term "transformation vector" means a construct capable of being transferred from one species to another.

"Naked DNA"

The vectors comprising nucleotide sequences encoding the agent of the present invention for use in treating collagen—related diseases may be administered directly as "a naked nucleic acid construct", preferably further comprising flanking sequences homologous to the host cell genome.

As used herein, the term "naked DNA" refers to a plasmid comprising a nucleotide sequences encoding an agent of the present invention together with a short promoter region to control its production. It is called "naked" DNA because the plasmids are not carried in any delivery vehicle. When such a DNA plasmid enters a host cell, such as a eukaryotic cell, the proteins it encodes are transcribed and translated within the cell.

Non-Viral Delivery

Alternatively, the vectors comprising nucleotide sequences of the present invention may be introduced into suitable host cells using a variety of non-viral techniques known in the art, such as transfection, transformation, electroporation and biolistic transformation.

As used herein, the term "transfection" refers to a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1,2,-bis (oleoyloxy)-3-(trimethylammonio) propane (DOTAP)-cholesterol complexes (Wolff and Trubetskoy 1998 Nature Biotechnology 16: 421) and combinations thereof.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Viral Vectors

Alternatively, the vectors comprising nucleotide sequences of the present invention may be introduced into suitable host cells using a variety of viral techniques which are known in the art, such as for example infection with recombinant viral vectors such as retroviruses, herpes simplex viruses and adenoviruses.

The vector may be a recombinant viral vectors. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10):1619–32). In the case of viral vectors, delivery of the nucleotide sequence encoding the agent is mediated by viral infection of a target cell.

Targeted Vector

The term "targeted vector" refers to a vector whose ability to infect/ransfect/transduce a cell or to be expressed in a host and/or target cell is restricted to certain cell types within the host organism, usually cells having a common or similar phenotype.

Replication Vectors

The nucleotide sequences encoding the agent of the present invention may be incorporated into a recombinant replicable vector. The vector may be used to replicate the nucleotide sequence in a compatible host cell. Thus in one embodiment of the present invention, the invention provides a method of making the agent of the present invention by introducing a nucleotide sequence of the present invention into a replicable vector, introducing the vector into a compatible host cell, and growing the host cell under conditions which bring about replication of the vector. The vector may be recovered from the host cell.

Expression Vector

Preferably, a nucleotide sequence of present invention which is inserted into a vector is operably linked to a control sequence that is capable of providing for the expression of the coding sequence, such as the coding sequence of the agent of the present invention by the host cell, i.e. the vector is an expression vector. The agent produced by a host recombinant cell may be secreted or may be contained intracellularly depending on the sequence and/or the vector used. As will be understood by those of skill in the art, expression vectors containing the agent coding sequences can be designed with signal sequences which direct secretion of the agent coding sequences through a particular prokaryotic or eukaryotic cell membrane.

Expression in vitro

The vectors of the present invention may be transformed or transfected into a suitable host cell and/or a target cell as described below to provide for expression of a target sequence of the present invention. This process may comprise culturing a host cell and/or target cell transformed with an expression vector under conditions to provide for expression by the vector of a coding sequence encoding the agent and optionally recovering the expressed agent. The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. The expression of the agent of the present invention may be constitutive such that they are continually produced, or inducible, requiring a stimulus to initiate expression. In the case of inducible expression, the production of the agent can be initiated when required by, for example, addition of an inducer substance to the culture medium, for example dexamethasone or IPTG.

Fusion Proteins

The agent of the present invention may be expressed as a fusion protein to aid in extraction and purification and/or delivery of the agent to an individual and/or to facilitate the development of a screen for agents capable of modulating the target sequence. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino orcarboxy terminus of the substance.

In another embodiment of the invention, the amino acid sequence may beligated to a heterologous sequence to encode a fusion protein. For example, for screening of peptide libraries for agents capable of affecting the substance activity, it may be useful to encode a chimeric substance expressing a heterologous epitope that is recognized by a commercially available antibody.

Host Cells

A wide variety of host cells can be employed for expression of the nucleotide sequences encoding the agent—such as a target sequenceof the present invention. These cells may be both prokaryotic and eukaryotic host cells. Suitable host cells include bacteria such as E. coli, yeast, filamentous fungi, insect cells, mammalian cells, typically immortalized, e.g., mouse, CHO, human and monkey cell lines and derivatives thereof.

Examples of suitable expression hosts within the scope of the present invention are fungi such as Aspergillus species (such as those described in EP-A-01 84438 and EP-A-0284603) and Trichoderma species; bacteria such as Bacillus species (such as those described in EP-A-0134048 and EP-A-0253455), Streptomyces species and Pseudomonas species; and yeasts such as Kluyveromyces species (such as those described in EP-A-0096430 and EP-A-0301670) and Saccharomyces species. By way of example, typical expression hosts may be selected from *Aspergillus niger, Aspergillus niger* var. tubigenis, *Aspergillus niger* var. awamori, *Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae.*

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Preferred host cells are able to process the expression products to produce an appropriate mature polypeptide. Examples of processing includes but is not limited to glycosylation, ubiquitination, disulfide bond formation and general post-translational modification.

Agent Isolation

The agent may be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the agent is secreted, it can be isolated from the supernatant in which the host cell is grown. If not secreted, the agent can be isolated from a lysate of the host cells.

Pharmaceutical Compositions

In one aspect, the present invention provides a pharmaceutical composition, which comprises an agent according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation oringestable solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

The invention further provides a method of preventing and/or treating diseases associated with scarring and/or fibrosis in an individual, the method comprising, for example, administering to an individual an agent which modulates activity of the target sequence. Such agents may be useful in, for example, the treatment of diseases associated with scarring and/or fibrosis such as, for example, cardiovascular disorders.

As used herein, the term "administered" includes but is not limited to delivery by a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, intracavernosal, subcutaneous, transdermal or intramuscular) route.

Typically the administration is via an oral route or typically by a topical injection or by an intracavernosal injection.

The agents of the present invention may be administered alone but will generally be administered in admixture with a suitable pharmaceutical excipient, diluent or carrier selected with regard to the intended route of administration and standard pharmaceutical practice.

For example, the agent can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The agent can also be administered parenterally, for example, intravenously, intra-arterially, intraperitoneally, intrathecally, intraventricularly, intraurethrally, intrasternally, intracranially, intramuscularly or subcutaneously, or it may be administered by infusion techniques. For such parenteral administration it is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The physician in any event will determine the actual dosage, which will be most suitable for any individual patient and will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the agent may be taken as a single dose as needed or desired.

The agent of the present invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the agent of the present invention can be administered in the form of a suppository or pessary, or it may be applied topically in the form of a gel, hydrogel, lotion, solution, cream, ointment or dusting powder. The agent of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Individual

As used herein, the term "individual" refers to vertebrates, particularly members of the mammalian species. The term includes but is not limited to domestic animals, sports animals, primates and humans.

Treatment

It is to be appreciated that all references herein to treatment include curative, palliative and prophylactic treatment.

Combination Therapy

The agent may be administered alone or in combination with other entities for the treatment of a disease associated with scarring and/or fibrosis which is associated with the target sequence. By way of example, the positive identification of an agent capable of modulating the target sequence using a screen may faciliate the use of combinatorial libraries to identify mimetics capable of acting in the same or a similiar manner. Such mimetics can be administered alone or in combination with other agents and/or therapeutics for the treatment of diseases associated with the target sequence of the present invention.

The agent of the present invention may be used in combination with other compositions and procedures for the treatment of a disease associated with scarring and/or fibrosis. By way of example, the agent may also be used in combination with other treatments of a disease associated with scarring and/or fibrosis which are currently in use.

By way of further example, an agent may be administered with another agent, such as at the same moment in time and at the same site. Alternatively, the agent may be delivered at a different time and to a different site. In one embodiment, the agent may even be delivered in the same delivery vehicle for the prevention and/or treatment of a disease associated with scarring and/or fibrosis.

Preferably the agent and/or combinations of agents and/or therapeutics thereof is/are administered simultaneously, separately or sequentialy.

Dosage

The dosage of the agent of the present invention will depend on the disease state or condition being treated and other clinical factors such as weight and condition of the individual and the route of administration of the compound. Depending upon the half-life of the agent in the particular individual, the agent can be administered between several times per day to once a week. It is to be understood that the present invention has application for both human and veterinary use. The methods of the present invention contemplate single as well as multiple administrations, given either simultaneously or over an extended period of time.

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

Preferably the compositions (or component parts thereof) of the present invention are administered orally.

In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof of the present invention may be administered by inhalation. In addition or in the alternative the compositions (or component parts thereof of the present invention may also be administered by one or more of: a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, intracavernosal, subcutaneous, transdermal or intramuscular) route.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Screens

Any one or more of the target sequences of the present invention may be used for identifying an agent capable of modulating the target sequence in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

Techniques for drug screening may be based on the method described in Geysen, European Patent Application 84/03564, published on Sep. 13, 1984. In summary, large numbers of different small peptide test compounds are synthesized on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Thus, the present invention relates to a method of identifying agents that modulate the target sequence the method comprising contacting a suitable target with the agent and then measuring the activity and/or levels of expression of the target sequence.

The present invention also relates to a method of identifying agents that selectively modulate the target sequence the method comprising contacting a suitable target with the agent and then measuring the activity and/or levels of expression of the target sequence.

Animal Models

In vivo models may be used to investigate and/or design therapies or therapeutic agents to treat a disease associated with scarring and/or fibrosis. The models could be used to investigate the effect of various tools/lead compounds on a target sequence.

The invention further provides transgenic nonhuman animals capable of expressing the nucleotide sequence encoding the target sequence of the present invention and/or a transgenic nonhuman animal having one or more nucleotide sequence encoding the target sequence of the present invention. Expression of such a nucleotide sequence is usually achieved by operably linking the nucleotide sequence to a promoter and optionally an enhancer, and microinjecting the construct into a zygote. See Hogan et al., "Manipulating the Mouse Embryo, A Laboratory Manual," Cold Spring Harbor Laboratory. Inactivation of such a nucleotide sequence may be achieved by forming a transgene in which a cloned nucleotide sequence is inactivated by insertion of a positive selection marker. See Capecchi, Science 244, 1288–1292 (1989). The transgene is then introduced into an embryonic stem cell, where it undergoes homologous recombination with an endogenous variant gene. Mice and other rodents are preferred animals. Such animals provide screens and/or screening systems for identifying agents capable of modulating a target sequence.

EXAMPLES

The invention will now be further described only by way of example in which reference is made to the following Figures.

FIGURES

FIG. 1a (labelled as Plate 1a) which shows a photographic representation;

FIG. 1b (labelled as Plate 1b) which shows a photographic representation;

FIG. 1c (labelled as Plate 1c) which shows a photographic representation;

FIG. 1d (labelled as Plate 1d) which shows a photographic representation;

FIG. 2a (labelled as Plate 2a) which shows a photographic representation;

FIG. 2b (labelled as Plate 2b) which shows a photographic representation;

FIG. 2c (labelled as Plate 2c) which shows a photographic representation;

FIG. 2d (labelled as Plate 2d) which shows a photographic representation;

FIG. 3a (labelled as Plate 3a) which shows a photographic representation;

FIG. 3b (labelled as Plate 3b) which shows a photographic representation;

FIG. 4a (labelled as Plate 4a) which shows a photographic representation;

FIG. 4b (labelled as Plate 4b) which shows a photographic representation;

FIG. 5a (labelled as Plate 5a) which shows a photographic representation;

FIG. 5b (labelled as Plate 5b) which shows a photographic representation;

FIG. 5c (labelled as Plate 5c) which shows a photographic representation;

FIG. 6 (labelled as Plate 6) which shows a photographic representation;

FIG. 7a (labelled as Plate 7a) which shows a photographic representation;

FIG. 7b (labelled as Plate 7b) which shows a photographic representation;

FIG. 7c (labelled as Plate 7c) which shows a photographic representation;

FIG. 7d (labelled as Plate 7d) which shows a photographic representation;

FIG. 8a (labelled as Plate 8a) which shows a photographic representation;

FIG. 8b (labelled as Plate 8b) which shows a photographic representation;

FIG. 8c (labelled as Plate 8c) which shows a photographic representation;

FIG. 8d (labelled as Plate 8d) which shows a photographic representation;

FIG. 9a (labelled as Plate 9a) which shows a photographic representation;

FIG. 9b (labelled as Plate 9b) which shows a photographic representation;

FIG. 10a (labelled as Plate 10a) which shows a photographic representation;

FIG. 10b (labelled as Plate 10b) which shows a photographic representation;

FIG. 11a (labelled as Plate 11a) which shows a photographic representation;

FIG. 11b (labelled as Plate 11b) which shows a photographic representation;

FIG. 11c (labelled as Plate 11c) which shows a photographic representation;

FIG. 11d (labelled as Plate 11d) which shows a photographic representation;

FIG. 12a (labelled as Plate 12a) which shows a photographic representation;

FIG. 12b (labelled as Plate 12b) which shows a photographic representation;

FIG. 12c (labelled as Plate 12c) which shows a photographic representation;

FIG. 12d (labelled as Plate 12d) which shows a photographic representation;

FIG. 13a (labelled as Plate 13a) which shows a photographic representation;

FIG. 13b (labelled as Plate 13b) which shows a photographic representation;

FIG. 13c (labelled as Plate 13c) which shows a photographic representation;

FIG. 14a (labelled as Plate 14a) which shows a photographic representation;

FIG. 14b (labelled as Plate 14b) which shows a photographic representation;

FIG. 14c (labelled as Plate 14c) which shows a photographic representation;

FIG. 14d (labelled as Plate 14d) which shows a photographic representation;

FIG. 15a (labelled as Plate 15a) which shows a photographic representation;

FIG. 15b (labelled as Plate 15b) which shows a photographic representation;

FIG. 15c (labelled as Plate 15c) which shows a photographic representation;

FIG. 15d (labelled as Plate 15d) which shows a photographic representation;

FIG. 16a (labelled as Plate 16a) which shows a photographic representation;

FIG. 16b (labelled as Plate 16b) which shows a photographic representation;

FIG. 17a (labelled as Plate 17a) which shows a photographic representation;

FIG. 17b (labelled as Plate 17b) which shows a photographic representation;

FIG. 17c (labelled as Plate 17c) which shows a photographic representation;

FIG. 17d (labelled as Plate 17d) which shows a photographic representation;

FIG. 18a (labelled as Plate 18a) which shows a photographic representation;

FIG. 18b (labelled as Plate 18b) which shows a photographic representation;

FIG. 18c (labelled as Plate 18c) which shows a photographic representation;

FIG. 18d (labelled as Plate 18d) which shows a photographic representation;

FIG. 19a (labelled as Plate 19a) which shows a photographic representation;

FIG. 19b (labelled as Plate 19b) which shows a photographic representation;

FIG. 19c (labelled as Plate 19c) which shows a photographic representation;

FIG. 19d (labelled as Plate 19d) which shows a photographic representation;

FIG. 20a (labelled as Plate 20a) which shows a photographic representation;

FIG. 20b (labelled as Plate 20b) which shows a photographic representation; and

FIG. 20c (labelled as Plate 20c) which shows a photographic representation.

EXAMPLE 1

Preparation of an antibody to the target sequence MER-AGPSFGQQR (SEQ ID No 1)

The antibody specific to PDE5al the long splice variant of PDE5 was raised using a synthetic peptide derived from the N-terminal sequence of human PDE5A1, i.e., MERAGPSFGQQR[C] (SEQ ID No 2), where [C] is a cysteine for conjugation—the peptide was conjugated to keyhole-limpet hemocyanin (adjuvent).

Rabbits were inoculated and received 4 subsequent bi-weekly booster injections prior to bleedout. The resulting antisera were affinity purified against the peptide antigen to yield LIP-1 antibody.

The rabbit polyclonal antibody LIP-1 was used at a dilution of 1:600, using an immunoperoxidase technique and DAKO rabbit Envision (cat. No. K4010) on formaline-fixed, paraffin-embedded sections of human tissue including corpus cavernosum, heart, skin prostate, liver, lung, bladder and peripheral vessels.

Results 1
Corpus Cavernosum

Plate 1.a: Photomicrograph of paraffin section of human corpus cavernosum. Immunohistochemistry with LIP-1 antibody.

This image is of human corpus cavernosum which is made up of vascular channels surrounded by irregular bundles of smooth muscle (m). The structure on the right is the urethra (u) which is lined by epithelial cells (ep). Beneath the urethral mucosa are numerous lymphatic channels (I) which are not surrounded by muscle. Note the positive (brown/red) staining of the smooth muscle cell bundles around the vascular channels (m). There is negative immunolocalisation of LIP-1 to the urethral (u) epithelial cells (ep) and to the lymphatic channels (I). (Original mag. ×10).

Plate 1.b: Photomicrograph of paraffin section of human corpus cavernosum. Negative control (no primary antibody). (Original mag. ×10).

Plate 1.c: Photomicrograph of paraffin section of human corpus cavernosum. Immunohistochemistry with LIP-1 antibody.

This is a low power image of a transverse section of the penis with a central urethra (u), and adjacent urethral duct (d) and smooth muscle bundles (m) adjacent to vascular spaces. Note the positive (brown/red) staining of the smooth muscle cells with negative staining for the epithelium of the urethra and urethral ducts.(Original mag. ×2)

Plate 1.d: Photomicrograph of paraffin section of human corpus cavernosum. Immunohistochemistrywith LIP-1 antibody.

This is a higher power image of Plate 1.c. Note the positive (brown/red) staining of the smooth muscle cells (m) with negative staining for the adjacent connective tissue elements and lymphatics (I). (Original mag. ×20)

Results 2
Bladder

Plate 2.a: Photomicrograph of paraffin section of human bladder. Immunohistochemistry with LIP-1 antibody.

This image is of human bladder which is composed of bundles of sub-mucosal smooth muscle (m). The structure on the right is the lumen of the bladder which is lined by epithelial cells (ep). Beneath the bladder mucosa are numerous lymphatic channels (I) which are not surrounded by muscle. Note the positive (brown/red) staining of the smooth muscle cell bundles (m) in the bladder wall. There is negative immunolocalisation of LIP-1 to the epithelial cells (ep) and lymphatic channels (I). (Original mag. ×10).

Plate 2.b: Photomicrograph of paraffin section of human bladder. Negative control (no primary antibody). (Original mag. ×10)

Plate 2.c: Photomicrograph of paraffin section of human bladder. Immunohistochemistrywith LIP-1 antibody.

Note the positive (brown/red) staining of the muscle cells (m) with negative staining for the epithelium (ep) and connective tissue elements. (Original mag. ×10).

Plate 2.d: Photomicrograph of paraffin section of human bladder. Immunohistochemistry with LIP-1 antibody. Note the positive (brown/red) staining of the muscle cells which can be seen to be nucleated at this power. (Original mag. ×20).

Results 3
Skin—Chronic Diabetic Ulcer

Plate 3.a: Photomicrograph of paraffin section of skin. This tissue is taken from the toe of a 54 year old male diabetic with chronic ischaemia and ulceration of the skin of two weeks duration. This section is taken from the edge of the ulcer.

Immunohistochemistry with LIP-1 antibody Hyperplastic but intact squamous epithelium (top) is negative. The underlying dermis contains mature scar tissue with small and large venules. Note the positive (brown/red) staining of the smooth muscle cells within the media of thevenules. (Original mag. ×10).

Plate 3.b: Photomicrograph of paraffin section of skin. The section is taken from border between the ulcer (left) and intact epithelium (right).

Immunohistochemistry with LIP-1 antibody Hyperplastic but intact squamous epithelium (right) and necrotic inflammatory exudate (left) is negative. Note the positive (brown/red) staining of the smooth muscle cells within the media of the venules (right) and of spindle cells within the base of the ulcer (left). (Original mag. ×20).

Plate 4.a: Photomicrograph of paraffin section of skin (as in 3.a. and 3.b). The section is taken from an intact area of dermis adjacent to the ulcer and shows an eccrine sweat gland and ducts. Immunohistochemistry with LIP-1 antibody. Note the positive (brown/red) staining of spindle cells (myoepithelial cells) surrounding the eccrine sweat gland and ducts with negative staining of the gland epithelial cells. (Original mag. ×20).

Plate 4.b: Photomicrograph of paraffin section of skin (as in 3.a. and 3.b). The section is taken from the healed ulcer base where fascicles of young scar tissue have replaced normal dermal structures. Immunohistochemistry with LIP-1 antibody. Note the positive (brown/red) staining of some of the spindle cells (myofibroblasts) and of some vascular structures. (Original mag. ×20).

Results 4
Skin—Chronic Diabetic Ulcer

Plate 5.a: Photomicrograph of paraffin section of skin (higher power view of 4.b). The section is taken from the healed ulcer base where fascicles of young scar tissue have replaced normal dermal structures.

Immunohistochemistry with LIP-1 antibody: Note the positive (brown/red) staining of some of the spindle cells (myofibroblasts) and of some of the microvessels which have a thin media (Original mag. ×40).

Plate 5.b: Photomicrograph of paraffin section of skin (higher power view of 5.a). The section is taken from the healed ulcer base where fascicles of young scar tissue have replaced normal dermal structures.

Immunohistochemistry with LIP-1 antibody Note the positive (brown/red) staining of some of the spindle cells (myofibroblasts) which are found amongst acellular collagen. In the cytoplasm of some of these spindle cells theimmunolocalisation has a patchy distribution. Note the positive (brown/red) staining of the medial smooth muscle cells within a small arteriole and the negative staining of the lining endothelial cells. Just above this arteriole there is a vascular structure (possibly a lymphatic) with no medial smooth muscle, which is negative. (Original mag. ×60).

Plate 5.c: Photomicrograph of paraffin section of skin (higher power view of 5.a). The section is taken from the healed ulcer base in an area of relatively cellular young scar tissue.

Immunohistochemistry with LIP-1 antibody Note the positive (brown/red) staining of some of the spindle cells (myofibroblasts). In some of these spindle cells the immunolocalisation has a patchy distribution. Note the positive (brown/red) staining of the medial smooth muscle cells within a small arteriole (centre) and the negative staining of the large lining endothelial cells.(Original mag. ×60)

Results 5

Pericardium—Coronary Artery

Plate 6: This image is of human pericardium showing the bifurcation point of a normal left anterior descending (LAD) coronary artery. Note the positive (brown/red) staining of the well organised arterial smooth muscle cells in the media (m) and the negative staining of the surrounding adventitial (a) connective tissue, negative endotheliual cells (E) and pericardial fat cells. Top right inset shows that the endothelial cells (E) of the artery are negative.

Top centre of the image, is a small lymphatic (no muscle) which is negative. At the top left hand corner there are some epicardial cardiac myocytes which are negative. The vessel in the bottom right corner is a coronary vein with irregularly arranged smooth muscle cell bundles in the media (m) which are positive and endothelial cells (E) which are negative. (Original mag. ×10).

Results 6

Pericardium—Coronary Vein

Plate 7.a: Photomicrograph of paraffin section of coronary vein in the pericardium.

Routine haematoxylin and eosin (H&E) staining. The lumen is top. The vein is lined by as single layer of endothelial cells. The media contains irregularly oriented smooth muscle cells and has no internal or external elastic lamina. The adventitia (lower) contains dense collagen. (Original mag. ×40).

Plate 7.b: Photomicrograph of paraffin section of coronary vein in the pericardium. Immunohistochemistry with CD31 antibody to endothelial cells Note the positive (brown/red) staining of the lining endothelial cells and capillary endothelial cells in the adventitia (Original mag. ×40).

Plate 7.c: Photomicrograph of paraffin section of coronary vein in the pericardium.

Immunohistochemistry with ASMA antibody to smooth muscle cells Note the positive (brown/red) staining of the smooth muscle cells in the media. (Original mag. ×40)

Plate 7.d: Photomicrograph of paraffin section of coronary vein in the pericardium.

Immunohistochemistry with LIP-1 antibody Note the positive (brown/red) staining of the smooth muscle cells in the media (cf. 7.c) and the negative staining of the lining endothelial cells (cf. 7.b). (Original mag. ×40).

Results 7

Pericardium—Coronary Venules, Arterioles and Lymphatics

Plate 8.a: Photomicrograph of paraffin section of the junction between the myocardium (lower) and pericardium (upper). Routine haematoxylin and eosin (H&E) staining. The myocardium (epicardium) consists of cardiac myocytes with intervening connective tissue elements and capillaries. The pericardium contains a small coronary artery branch (upper field) and a small coronary vein (centre) surrounded by mature adipose tissue, capillaries and lymphatics. (Original mag. ×20).

Plate 8.b: Photomicrograph of paraffin section of the junction between the myocardium (lower) and pericardium (upper). Immunohistochemistry with CD31 antibody to endothelial cells. Note the positive (brown/red) staining of the lining endothelial cells of the intramyocardial and pericardial capillaries, the small coronary artery branch (upper field), small coronary vein (centre) and lymphatics. (Original mag. ×20).

Plate 8.c: Photomicrograph of paraffin section of the junction between the myocardium (lower) and pericardium (upper).

Immunohistochemistry with ASMA antibody to smooth muscle cells Note the positive (brown/red) staining of the media of the small coronary artery branch (upper field) and small coronary vein (centre) with negative staining of capillaries, lymphatics and cardiac myocytes. (Original mag. ×20).

Plate 8.d: Photomicrograph of paraffin section of the junction between the myocardium (lower) and pericardium (upper).

Immunohistochemistry with LIP-1 antibody Note the positive (brown/red) staining of the media of the small coronary artery branch (upper field) and small coronary vein (centre) with negative staining of capillaries, lymphatics and cardiac myocytes (cf. 8.c). (Original mag. ×20).

Results 8

Epicardium—Coronary Venules, Arterioles, Capillaries and Lymphatics

Plate 9.a: Photomicrograph of paraffin section of the junction between the myocardium (lower) and pericardium (upper).

Immunohistochemistry with LIP-1 antibody Note the positive (brown/red) staining of the media of the small coronary artery branch (upper field) and small coronary vein (centre) with negative staining of capillaries, lymphatics and cardiac myocytes (cf. 8.c). (Original mag. ×20).

Plate 9.b: Photomicrograph of paraffin section of the junction between the myocardium (lower) and pericardium (upper). Adjacent section to 9.a. Negative control (no primary antibody).

Note the negative staining of the media of the small coronary artery branch (upper field) and small coronary vein (centre) with negative staining of capillaries, lymphatics and cardiac myocytes. (Original mag. ×20).

Plate 10.a: Photomicrograph of paraffin section of the normalepicardium.

Immunohistochemistry with CD31 antibody to endothelial cells Note the positive (brown/red) staining of the lining endothelial cells of the normal intramyocardial capillaries between the negatively stained myocytes and of the endothelial cells lining a small arteriole (centre). (Original mag. ×40).

Plate 10.b: Photomicrograph of paraffin section of the normal epicardium (adjacent section to 10.a).

Immunohistochemistry with LIP-1 antibody Note the positive staining of the medial smooth muscle cells only of the arteriole (centre) and the negative staining of the endothelial cells of the intramyocardial capillaries and the cardiac myocytes. (Original mag. ×40).

Results 9
Myocardium
Plate 11.a: Photomicrograph of paraffin section of human heart.

Immunohistochemistry with LIP-1 antibody This image is of human heart which is made up of cardiac myocytes (m). Within the connective tissue elements of the heart there are small arteries and arterioles (a), veins (v) and lymphatics (I). Note the positive (brown/red) staining of the smooth muscle cells in the media of thearteries (a) and the veins (v). The cardiac myocytes (m) are negative. There is negative immunolocalisation of LIP-1 to the lymphaticchannels (I). (Original mag. ×10).

Plate 11.b: Photomicrograph of paraffin section of human heart. Negative control (no primary antibody). (Original mag. ×10).

Plate 11.c: Photomicrograph of paraffin section of human heart.

Immunohistochemistry with LIP-1 antibody This image is of human heart which is made up of cardiac myocytes (m). Within the connective tissue elements of the heart there are small arterioles (a). Note the positive (brown/red) staining of the smooth muscle cells in the media of the arterioles (a). The cardiacmyocytes (m) are negative. (Original mag. ×20).

Plate 11.d: Photomicrograph of paraffin section of human heart. Immunohistochemistry with LIP-1 antibody. This image is of human heart showing cardiac myocytes (m) surrounding a central intramyocardial coronary artery branch (a). Note the positive (brown/red) staining of the smooth muscle cells in the media of this artery (a) and the negative adjacent cardiac myocytes (m). (Original mag. ×20).

Results 10
Myocardium
Plate 12.a: Photomicrograph of paraffin section of the myocardium. Immunohistochemistry with LIP-1 antibody Note the positive (brown/red) staining of the media of the small coronary arteriole (centre) with negative staining of the lining endothelial cells and of the surrounding cardiac myocytes. (Original mag. ×60).

Plate 12.b: Photomicrograph of paraffin section of the myocardium.

Immunohistochemistry with LIP-1 antibody Note the positive (brown/red) staining of the media of the small coronary arteriole (centre) with negative staining of the lining endothelial cells, adventitia and surrounding cardiac myocytes. (Original mag. ×60).

Plate 12.c: Photomicrograph of paraffin section of a lymphatic (lower) and portion of an artery (upper) in the pericardium.

Immunohistochemistry with LIP-1 antibody Note the positive (brown/red) staining of the media of the coronary artery media (upper) with negative staining of the lining endothelial cells of the lymphatic (lower) (Original mag. ×60).

Plate 12.d: Photomicrograph of paraffin section of a coronary vein in the pericardium. Immunohistochemistry with LIP-1 antibody Note the positive (brown/red) staining of irregular groups of smooth muscle cells in the media with negative staining of the lining endothelial cells. (Original mag. ×60).

Results 11
Organising Ischaemic Myocardium
Plate 13.a: Photomicrograph of paraffin section of organising myocardial infarction (granulation tissue) in the epicardium.

Immunohistochemistry with CD31 antibody to endothelial cells Note the positive (brown/red) staining of the lining endothelial cells of the established arteriole centre, lower) and the capillaries and new vessels in the granulation tissue, venules and lymphatics. (Original mag. ×20).

Plate 13.b: Photomicrograph of paraffin section of organising myocardial infarction (granulation tissue) in the epicardium (adjacent section to 13.a).

Immunohistochemistry with ASMA antibody to smooth muscle cells Note the positive (brown/red) staining of the medial smooth muscle cells of the established arteriole (centre, lower) and venules within the granulation tissue with negative staining of capillaries and lymphatics. (Original mag. ×20).

Plate 13.c: Photomicrograph of paraffin section of organising myocardial infarction (granulation tissue) in the epicardium (adjacent section to 13.b).

Immunohistochemistry with LIP-1 antibody: Note the positive (brown/red) staining of the medial smooth muscle cells of the established arteriole (centre, lower) and venules within the granulation tissue with negative staining of capillaries and lymphatics. (Original mag. ×20).

Results 12
Confocal Fluorescence Microscopy—Cardiac Myocytes, Endocardium & Epicardial Vessels
Plate 14.a: Photomicrograph of a 4% paraformaldehyde perfusion-fixed section of human heart. Within the normal myocardium there is a small arteriole (600 pm in diameter) (see Plate 12.a). LIP-1 is localised with fluorescein (green) and CD31 (endothelial cell marker) is localised with Texas Red (red).The section is cross-cut but shows distinct staining of the endothelial cells with no co-localisation with LIP-1. LIP-1 has a localisation to medial smooth muscle cells with a striated pattern of staining. Surrounding cardiac myocytes are negative for LIP-1.

Plate 14.b: Photomicrograph of a 4% paraformaldehyde perfusion-fixed section of human heart. Within the normal epicardium there is a normal coronary artery branch (see Plate 8.a).

LIP-1 is localised with fluorescein (green) and CD31 (endothelial cell marker) is localised with Texas Red (red). Note the auto-fluorescentelastin of the internal elastic lamina (apple-green) between the intima and media. Perfusion fixation has preserved most of the lining endothelial cells which show distinct staining with CD31 (red) with no co-localisation with LIP-1. LIP-1 (green) has a typical localisation to medial smooth muscle cells with a striated pattern of staining. Adjacent collegen and elastin within the epicardium shows apple-green autofluorescence.

Plate 14.c: Photomicrograph of a 4% paraformaldehyde perfusion-fixed section of ischaemic human heart. Within the thickened endocardium there is a proliferation of smooth muscle cells and myofibroblasts. LIP-1 is localised with fluorescein (green) and alpha smooth muscle actin (ASMA) (smooth muscle cell (SMC) marker) is localised with Texas Red (red). Most of the cells show colocalisation (yellow) of LIP-1 (green) and ASMA (red) (see also Plates 17.d and 19.a). The ischaemic myocardium below (see 14.d) shows single spindle cell staining within scar tissue.

Plate 14.d: HigHer power view of the sub-endocardial iscahemic myocardium in seen in Plate 14.c. LIP-1 is localised with fluorescein (green) and alpha smooth muscle actin (ASMA) (smooth muscle cell (SMC) marker) is localised with Texas Red (red). Single spindle cell staining of either LIP-1 or ASMA is seen within scar tissue.

Results 13
Endocardium
Plate 15.a: Photomicrograph of paraffin section of the left atrium in a patient with heart failure. Routine haematoxylin and eosin (H&E) staining. The endocardium is thickened (lower), there is cardiac myocyte hypertrophy (centre). The pericardium contains abundant adipose tissue (top). (Original mag. ×10).

Plate 15.b: Photomicrograph of paraffin section of the left atrium in a patient with heart failure (adjacent section to 15.a).

Immunohistochemistry with CD31 antibody to endothelial cells Note the positive (brown/red) staining of some remaining intact endocardial lining endothelial cells (lower), of the intramyocardial and pericardial capillaries, the small coronary artery branch (upper field), small coronary veins and lymphatics. (Original mag. ×10).

Plate 15.c: Photomicrograph of paraffin section of the left atrium in a patient with heart failure (adjacent section to 15.b).

Immunohistochemistry with ASMA antibody to smooth muscle cells Note the positive (brown/red) staining of spindle cells within the thickened endocardium (lower field), within smooth muscle cells in the media of arterioles and veins and some non-specific staining of hypertrophied cardiac myocytes (lower field). (Original mag. ×10).

Plate 15.d: Photomicrograph of paraffin section of the left atrium in a patient with heart failure (adjacent section to 15.c).

Immunohistochemistry with LIP-1 antibody Note the positive (brown/red) staining of the media of the small intramyocardial coronary artery branch (upper, centre field) and of spindle cells (SMCs and myofibroblasts) within the thickened endocardium (lower field) and the negative staining of cardiacmyocytes. (Original mag. ×10).

Results 14
Endocardium

Plate 16.a: Photomicrograph of paraffin section of the left atrium in a patient with heart failure.

Immunohistochemistry with LIP-1 antibody Note the positive (brown/red) staining of the media of the small intramyocardial coronary artery branch (upper, centre field) and of spindle cells (SMCs and myofibroblasts) within the thickened endocardium (lower field) and the negative staining of cardiacmyocytes (cf. 15.c). (Original mag. ×10).

Plate 16.b: Photomicrograph of paraffin section of the left atrium in a patient with heart failure. Adjacent section to 16.a. Negative control (no primary antibody). Note the negative staining of the media of the smallintramyocardial coronary artery branch (upper, centre field) and of spindle cells (SMCs and myofibroblasts) within the thickened endocardium (lower field) and the negative staining of cardiac myocytes.(Original mag. ×10).

Results 15
Endocardium

Plate 17.a: Photomicrograph of paraffin section of endocardium (lower) from the left ventricle in a patient with heart failure.

Immunohistochemistry with LIP-1 antibody Note the negative staining of cardiac myocytes and the positive (brown/red) staining of the spindle cells in the media of the arteries and the veins and within the thickened endocardium. (Original mag. ×10).

Plate 17.b: Photomicrograph of paraffin section of endocardium (lower) from the left ventricle in a patient with heart failure.

Immunohistochemistry with LIP-1 antibody Note the negative staining of cardiac myocytes (upper field), negative staining of the endothelial cells lining the endocardium and the positive (brown/red) staining of the spindle cells within the thickened endocardium. (Original mag. ×40).

Plate 17.c: Photomicrograph of paraffin section of endocardium (lower) from the left ventricle in a patient with heart failure.

Immunohistochemistry with LIP-1 antibody Note the negative staining of cardiac myocytes (upper field), negative staining of the endothelial cells lining the endocardium and the positive (brown/red) staining of the spindle cells within the thickened endocardium. (Original mag. ×60).

Plate 17.d: Photomicrograph of paraffin section of endocardium (lower) from the left ventricle in a patient with heart failure.

Immunohistochemistry with LIP-1 antibody: Note the negative staining of the endothelial cells lining the endocardium and the positive (brown/red) staining of the spindle cells within the thickened endocardium. (Original mag. ×60).

Results 16
Endocardium—Double Immunohistochemistry (LIP-1/vWF)

Plate 18.a: Photomicrograph of paraffin section of endocardium from the left ventricle in a patient with heart failure. Immunohistochemistry with LIP-1 antibody (NBT—purple) and Factor VIII/vWF (DAB-brown): Note the negative staining of cardiac myocytes (right). Factor VIII/vWF (brown) staining of the endothelial cells lining the endocardium is seen (left) with distinct LIP-1 (purple) staining of the spindle cells within the thickened endocardium (centre). (Original mag. ×40).

Plate 18.b: Photomicrograph of paraffin section of endocardium from the left ventricle in a patient with heart failure.

Immunohistochemistry with LIP-1 antibody (purple) and Factor VIII/vWF (brown): Note the negative staining of cardiac myocytes (right). Factor VIII/vWF (brown) staining of the endothelial cells lining the endocardium is seen (left) with distinct LIP-1 (purple) staining of the spindle cells within the thickened endocardium (centre). (Original mag. ×60).

Plate 18.c: Photomicrograph of paraffin section of a focus offibrotic myocardium from left ventricle in a patient with heart failure. Two small arterioles are seen within healed scar tissue.

Immunohistochemistry with LIP-1 antibody (purple) and Factor VIII/vWF (brown): CD31 (brown) staining of the endothelial cells lining the arterioles are seen. LIP-1 (purple) staining of the smooth muscle cells in the arteriolar media and surrounding spindle cells within the the scar tisue are seen (lower field). (Original mag. ×60).

Plate 18.d: Photomicrograph of paraffin section of endocardium from the left ventricle in a patient with heart failure.

Immunohistochemistry with LIP-1 antibody (purple) and Factor VIII/vWF (brown): Note the negative staining of cardiacmyocytes (left). FactorVIII/vWF (brown) staining of the endothelial cells lining a small capillary is seen (centre) with distinct LIP-1 (purple) staining of the spindle cells within the thickened endocardium (right). (Original mag. ×60).

Results 17
Endocardium—Double Immunohistochemistry (LIP-1/ASMA)

Plate 19.a: Photomicrograph of paraffin section of endocardium from the left ventricle in a patient with heart failure.

Immunohistochemistry with LIP-1 antibody (NBT—purple) and ASMA (DAB—brown): Within the thickened endocardium, ASMA (brown) staining of a population of spindle cells is seen (left) with distinct LIP-1 (purple) staining of other spindle cells. (Original mag. ×40).

Plate 19.b: Photomicrograph of paraffin section of endocardium from the left ventricle in a patient with heart failure (higher power view of 19.a).

Immunohistochemistry with LIP-1 antibody (purple) and ASMA (brown) Within the thickened endocardium, ASMA (brown) staining of a population of spindle cells is seen (left) with distinct LIP-1 (purple) staining of other spindle cells and co-localisation (brown/purple) of some cells. (Original mag. ×60).

Plate 19.c: Photomicrograph of paraffin section of endocardium from the left ventricle in a patient with heart failure.

Immunohistochemistry with LIP-1 antibody (purple) and ASMA (brown) Within the thickened endocardium the spindle cells are sectioned transversely. ASMA (brown) staining of a population of cells is seen (left) with distinct LIP-1 (purple) staining of other spindle cells and co-localisation (brown/purple) of some cells. (Original mag. ×60).

Plate 19.d: Photomicrograph of paraffin section of a focus offibrotic myocardium from left ventricle in a patient with heart failure. A small arteriole is seen (centre) surrounded by lymphocytes within healing scar tissue.

Immunohistochemistry with LIP-1 antibody (purple) and ASMA (brown) ASMA (brown) staining of medial smooth muscle cells is seen with co-localisation of LIP-1 (purple) staining of medial smooth muscle cells and negative staining of lining endothelial cells and surrounding lymphocytes. (Original mag. ×60).

Results 18
Hypertensive Arteriolosclerosis/Diffuse Intimal Thickening

Plate 20.a: Photomicrograph of paraffin section of a peripheral artery. The vessel lumen is on the left. There is diffuse intimal thickening with spindle cells expanding the intima. The media (centre) is intact. The adventitia (right) is normal.

Immunohistochemistry with CD31 antibody to endothelial cells Note the positive (brown/red) staining of the lining endothelial cells of the artery (left) and thevasa vasorum in the adventitia (right). (Original mag. ×20).

Plate 20.b: Photomicrograph of paraffin section of a peripheral artery (adjacent section to 20.a).

Immunohistochemistry with ASMA antibody to smooth muscle cells (SMC): Note the strongly positive (brown/red) staining of the intact media (centre) and the media of the vasa vasorum in the adventitia (right). Within the thickened intima (left) positive spindle cells are present. (Original mag. ×20).

Plate 20.c: Photomicrograph of paraffin section of a peripheral artery (adjacent section to 20.b).

Immunohistochemistry with LIP-1 antibody. There is strongly positive, equally strong(brown/red) staining of the spindle cells of the intact media (centre), the media of the vasa vasorum in the adventitia (right) and the spindle cells within the thickened intima. (Original mag. ×20).

Results 19
Myoepithelial Cells

The above mentioned antibody was also found to be able to identify the targeton myoepithelial cells.

Discussion

Results 1–18 demonstrate that the target sequence of the present invention is selectively expressed by cells expressing a smooth muscle phenotype—in particular smooth muscle cells and myofibroblasts and myoepithelial cells—from human tissue samples including but not limited to corpus cavernosum, heart, skin prostate, liver, lung, bladder and peripheral blood vessels. Thus, the present invention provides for a method of identification of these cell types in normal and diseased tissue samples.

Summary

In summation, the present invention provides an isolated target sequence. The target sequence is a splice variant of PDE5 called a PDE5a1, a component of which is presented as SEQ ID No 1. The identified target sequence of the present invention may be used to as a target to identify agents (such as modulators) useful in the prevention and/or treatment of a disease associated with scarring and/or fibrosis or to selectively identify cell with a smooth muscle phenotype—in particular smooth muscle cells and myofibroblasts and myoepithelial cells—in sample of normal and diseased tissue from individuals.

In particular, the present invention also provides methods and means for diagnosing a disease associated with scarring and/or fibrosis or a predisposition to a disease associated with scarring and/or fibrosis by identifying the presence of a target sequence in a cell or tissue extract from an individual. These presence or absence of a target sequence may be associated either directly or indirectly with predisposition to a range of disease associated with scarring and/or fibrosis such as cardiovascular diseases and fibrotic diseases.

The identified target sequence of the present invention may be used to as a target for the identification of agents (such as modulators) which may be used to prevent and/or delay the onset of a disease associated with scarring and/or fibrosis. By way of example, an identified agent, such as an antibody may be used to selectively identify cells expressing a smooth muscle phenotype—in particular smooth muscle cells and myofibroblasts and myoepithelial cells—in samples of normal and diseased tissue from individuals. Methods of treatment, kits for diagnostic purposes and an isolated target sequence are also described as well as methods of isolating agents capable of modulating the target sequence.

Part of the assay methods or processes as described herein may be performed in silico by use of suitable computational software. The present invention also encompasses any data set generated by such methods or processes. The data set may be used in a drug development program.

Hence, other aspects of the present invention include: a A method for predicting, simulating or modelling the molecular characteristics and/or molecular interactions of an agent with a target sequence presented as SEQ ID No 1 or an analogue thereof comprising the use of a computer model, said computer model comprising, using, or depicting the sequence presented as SEQ ID No. 1 to provide an image of said binding ligand domain and to optionally display said image.

Typically the method further comprises providing an image of said agent in association with the sequence presented as SEQ ID No. 1 and optionally displaying said image.

For preferred embodiments the agent is manufactured and optionally formulated as a pharmaceutical composition.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be covered by the present invention.

What is claimed is:

1. An isolated target sequence, wherein said target sequence is comprising a polypeptide consisting of the sequence shown in SEQ ID NO:1.

2. The isolated target sequence of claim 1 wherein said target sequence is immunologically reactive with an antibody.

* * * * *